(12) United States Patent
Murakawa et al.

(10) Patent No.: US 9,314,186 B2
(45) Date of Patent: Apr. 19, 2016

(54) BODY FAT MEASUREMENT DEVICE

(71) Applicants: Yasuaki Murakawa, Kyoto (JP);
Takehiro Hamaguchi, Kyoto (JP);
Kazuhisa Tanabe, Kyoto (JP);
Hiromichi Karo, Kyoto (JP)

(72) Inventors: Yasuaki Murakawa, Kyoto (JP);
Takehiro Hamaguchi, Kyoto (JP);
Kazuhisa Tanabe, Kyoto (JP);
Hiromichi Karo, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 505 days.

(21) Appl. No.: 13/712,066

(22) Filed: Dec. 12, 2012

(65) Prior Publication Data
US 2013/0102870 A1 Apr. 25, 2013

Related U.S. Application Data

(63) Continuation of application No. PCT/JP2011/066337, filed on Jul. 19, 2011.

(30) Foreign Application Priority Data

Jul. 22, 2010 (JP) ................................. 2010-165160

(51) Int. Cl.
*A61B 5/053* (2006.01)
*A61B 5/00* (2006.01)

(52) U.S. Cl.
CPC .............. *A61B 5/0537* (2013.01); *A61B 5/4872* (2013.01); *A61B 5/6823* (2013.01); *A61B 5/6825* (2013.01); *A61B 5/6829* (2013.01); *A61B 5/6831* (2013.01); *A61B 5/7278* (2013.01)

(58) Field of Classification Search
CPC .... A61B 5/053; A61B 5/0537; A61B 5/4869; A61B 5/4872; A61B 5/6801; A61B 5/6823; A61B 5/6825; A61B 5/6828; A61B 5/6829; A61B 5/6831; A61B 5/6835; A61B 2560/0468; A61B 2562/0209; A61B 2562/046
USPC .......... 600/386, 372, 382, 390, 393, 547, 384
See application file for complete search history.

(56) References Cited

U.S. PATENT DOCUMENTS 5,615,688 A * 4/1997 O'Dwyer ............. A61B 5/1135
600/534
6,640,460 B1 * 11/2003 Nabarro ................... A41C 5/00
33/512

(Continued)

FOREIGN PATENT DOCUMENTS

CN 101316554 A 12/2008
JP 2002-369806 A 12/2002

(Continued)

OTHER PUBLICATIONS

International Search Report issued in corresponding International Application No. PCT/JP2011/066337 dated Aug. 30, 2011, and English translation thereof (2 pages).

(Continued)

*Primary Examiner* — Lee S Cohen
*Assistant Examiner* — Erin M Cardinal
(74) *Attorney, Agent, or Firm* — Osha Liang LLP

(57) ABSTRACT

A body fat measurement device includes a plurality of electrodes including back area electrodes and upper limb electrodes, a body impedance measurement unit that measures a body impedance using the plurality of electrodes, a body composition information calculation unit that calculates a body fat mass based on the body impedance, a fitting belt for bringing the back area electrodes into contact with the surface of the measurement subject's back area in a pressurized state, and an upper limb unit that includes a gripping portion that can be gripped by the measurement subject's hand, the upper limb electrodes being provided in the gripping portion. The upper limb unit can be attached to and detached from the fitting belt.

10 Claims, 16 Drawing Sheets

(56) References Cited

U.S. PATENT DOCUMENTS

| | | | |
|---|---|---|---|
| 2002/0151815 A1* | 10/2002 | Kawanishi | A61B 5/0537 600/547 |
| 2004/0077969 A1* | 4/2004 | Onda et al. | 600/547 |
| 2005/0059903 A1* | 3/2005 | Izumi | 600/547 |
| 2005/0107717 A1* | 5/2005 | Yamamoto et al. | 600/547 |
| 2005/0222516 A1* | 10/2005 | Kasahara et al. | 600/547 |
| 2005/0234308 A1* | 10/2005 | Naukkarinen | A61B 5/0537 600/300 |
| 2006/0235327 A1* | 10/2006 | Masuo et al. | 600/547 |
| 2006/0282005 A1* | 12/2006 | Kasahara et al. | 600/547 |
| 2007/0038140 A1* | 2/2007 | Masuo et al. | 600/547 |
| 2007/0175007 A1* | 8/2007 | Chan | A44B 11/001 24/614 |
| 2008/0021349 A1* | 1/2008 | Sakai | A61B 5/1079 600/587 |
| 2009/0089672 A1* | 4/2009 | Tseng et al. | 715/700 |
| 2009/0182243 A1* | 7/2009 | Oku et al. | 600/547 |
| 2009/0247896 A1* | 10/2009 | Kanai et al. | 600/547 |
| 2009/0264790 A1* | 10/2009 | Ashida et al. | 600/547 |
| 2011/0130676 A1* | 6/2011 | Murakawa | A61B 5/0537 600/547 |
| 2012/0172747 A1* | 7/2012 | Fukuda et al. | 600/547 |
| 2012/0310068 A1* | 12/2012 | Karo et al. | 600/384 |
| 2012/0330181 A1* | 12/2012 | Takahashi et al. | 600/547 |

FOREIGN PATENT DOCUMENTS

| | | |
|---|---|---|
| JP | 2007-014664 A | 1/2007 |
| JP | 2010-069249 A | 4/2010 |
| WO | 2010/032835 A1 | 3/2010 |

OTHER PUBLICATIONS

Patent Abstracts of Japan, Publication No. 2002-369806, Published on Dec. 24, 2002, 1 page.

Patent Abstracts of Japan, Publication No. 2007-014664, Published on Jan. 25, 2007, 1 page.

Patent Abstracts of Japan, Publication No. 2010-069249, Published on Apr. 2, 2010, 1 page.

Office Action issued in corresponding Chinese Application No. 201180035835.5 dated Jul. 25, 2014, and English translation thereof (25 pages).

* cited by examiner

BODY FAT MEASUREMENT DEVICE

TECHNICAL FIELD

The present invention relates to body fat measurement devices configured so as to be capable of calculating the body fat mass of a measurement subject by measuring a body impedance, and particularly relates to body fat measurement devices configured so as to be capable of easily measuring a visceral fat mass and/or a subcutaneous fat mass in households or the like.

BACKGROUND ART

Body fat mass is known as one index used for determining the health of a measurement subject. In particular, a visceral fat mass is known as an index used for determining whether or not a measurement subject suffers from central obesity. Central obesity is said to bring about lifestyle-related diseases that can easily lead to artery hardening, such as diabetes, hypertension, and hyperlipidemia. The aforementioned indexes hold promise in terms of preventing such diseases.

"Visceral fat" refers to fat that builds up in the periphery of the internal organs, and is located on the inner sides of the abdominal muscles and back muscles. Visceral fat is distinguished from subcutaneous fat, which is located in the surface layers of the trunk area. It is typical to employ the area occupied by visceral fat in a cross-section of the trunk area that corresponds to the navel (referred to as a "visceral fat cross-sectional area" hereinafter) as an indicator of the visceral fat mass.

Normally, visceral fat mass is measured by analyzing images obtained through X-ray computed tomography (CT), magnetic resonance imaging (MRI), or the like. In this image analysis, a tomographic image of the trunk area is obtained through the X-ray CT or the like, and the visceral fat cross-sectional area is calculated geometrically from the cross-sectional image.

X-ray CT machines are installed in most medical facilities, and it is difficult to measure a visceral fat mass on a daily basis using the stated image analysis technique. Furthermore, because X-ray CT and the like obtain tomographic images using radiation, it is undesirable to measure the visceral fat mass on a daily basis using X-ray CT and the like.

A body impedance technique is being considered as a method for measuring a body fat mass, as an alternative to image analysis using X-ray CT or the like. In the body impedance technique, electrodes are placed in contact with the four limbs, and a body impedance is measured using those electrodes. The body fat mass is then calculated based on the body impedance.

A body fat measurement device that uses the body impedance technique makes it possible to accurately measure the extent of body fat buildup throughout the entire body or in specific areas such as the four limbs, the trunk area, or the like. However, conventional body fat measurement devices that use the body impedance technique affix electrodes only to the four limbs, as mentioned above. Conventional body fat measurement devices that use the body impedance technique thus cannot make accurate measurements by extracting the extent of visceral fat building, the extent of subcutaneous fat buildup, and so on.

JP 2002-369806A (Patent Literature 1) discloses a technique related to a body fat measurement device. In this body fat measurement device, electrodes are provided on the inner circumferential surface of a belt member. The belt member is affixed to a measurement subject's trunk area, and thus the electrodes are placed in contact with the trunk area.

Meanwhile, JP 2007-014664A (Patent Literature 2) discloses a technique related to a body fat measurement device. In this body fat measurement device, a fitting unit that is fitted onto a measurement subject's trunk area and a lower limb unit onto which the measurement subject steps are configured as separate units. Abdominal area electrodes and handle portions are provided in the fitting unit, and hand electrodes are provided in the handle portions. Foot electrodes are provided in the lower limb unit. By gripping the handle portions with his/her hands, the measurement subject brings the hand electrodes into contact with his/her palms. Then, by pressing the fitting unit against his/her abdominal area using his/her hands that grip the handles, the measurement subject brings the abdominal area electrodes into contact with his/her abdominal area. The measurement subject then brings the foot electrodes into contact with the soles of his/her feet by stepping onto the lower limb unit.

SUMMARY OF INVENTION

In order to realize a body fat measurement device configured to be capable of easily and accurately calculating visceral fat mass and subcutaneous fat mass at home using the body impedance technique, it is extremely important to meet the following two conditions: one, that the measurement can be performed easily through simple operations; and two, that the measurement subject can perform the measurement him/herself without help from an assistant or the like.

However, it is necessary to place electrodes in contact with the measurement subject's back without placing electrodes in contact with the measurement subject's abdominal area and to place electrodes in contact with the hands and feet of the measurement subject in order to calculate the visceral fat mass and the subcutaneous fat mass in a more accurate manner. One of the reasons for this is that the subcutaneous fat that accumulates on the abdominal area side is relatively thinner than the subcutaneous fat that accumulates on the back area side, and thus if the electrodes are placed in contact with the abdominal area, the current that is applied will flow through fat-free areas, which makes it easy for errors to occur.

However, the body fat measurement device disclosed in the stated Patent Literature 1 does not take into consideration placing electrodes in contact with the hands and feet, whereas the body fat measurement device disclosed in the stated Patent Literature 2 does not take into consideration placing electrodes in contact with the back. Thus, it is necessary to make some kind of improvement in order to realize a body fat measurement device capable of easily and accurately calculating a visceral fat mass and a subcutaneous fat mass at home.

Therefore, one or more embodiments of the present invention provide a body fat measurement device capable of easily and accurately measuring body fat masses, such as visceral fat mass, even at home.

A body fat measurement device according to one or more embodiments of the present invention includes: a plurality of electrodes including back area electrodes for making contact with the surface of a back area that is an area on the back side of a measurement subject's trunk area and upper limb electrodes for making contact with the surface of the measurement subject's upper limbs; a body impedance measurement unit that measures a body impedance of the measurement subject's body using the plurality of electrodes; a body composition information calculation unit that calculates a body fat mass based on the body impedance measured by the body impedance measurement unit; a fitting belt for bringing the back area electrodes into contact with the surface of the measurement subject's back area in a pressurized state by being tightened around the measurement subject's trunk area; and an upper limb unit that includes a gripping portion that can be gripped by the measurement subject's hand, the upper limb electrodes being provided in the gripping portion. Here, the upper limb unit can be attached to and detached from the fitting belt.

A body fat measurement device according to one or more embodiments of the present invention is the body fat measurement device according to the stated first aspect, in which the fitting belt includes a first engagement member; the upper limb unit includes a second engagement member that can engage with the first engagement member; the upper limb unit is attached to the fitting belt by the first engagement member entering an engaged state with the second engagement member; and the upper limb unit can be detached from the fitting belt by canceling the engaged state.

In a body fat measurement device according to one or more embodiments of the present invention, the first engagement member forms an opening by being attached to the fitting belt; the second engagement member has a predetermined length that enables the second engagement member to be inserted into the opening; the upper limb unit is attached to the fitting belt by the second engagement member being inserted into the opening; and the upper limb unit is detached from the fitting belt by the second engagement member being pulled out from the opening.

In a body fat measurement device according to one or more embodiments of the present invention, the position at which the first engagement member is attached to the fitting belt can be moved along the lengthwise direction of the fitting belt.

In a body fat measurement device according to one or more embodiments of the present invention, the upper limb unit includes a display unit that can display body composition information including the body fat mass calculated by the body composition information calculation unit.

In a body fat measurement device according to one or more embodiments of the present invention, the upper limb unit includes an operating unit for accepting an instruction from the measurement subject.

In a body fat measurement device according to one or more embodiments of the present invention, the plurality of electrodes further includes lower limb electrodes for making contact with the surfaces of the measurement subject's lower limbs; and the body fat measurement device further includes a lower limb unit for bringing the lower limb electrodes into contact with the soles of the measurement subject's feet when the measurement subject steps onto the lower limb unit.

In a body fat measurement device according to one or more embodiments of the present invention, the upper limb unit and the fitting belt are electrically connected to each other via a wire; and one of the upper limb unit and the fitting belt is electrically connected to the lower limb unit via a wire.

In a body fat measurement device according to one or more embodiments of the present invention, connection cables that connect the upper limb unit, the fitting belt, and the lower limb unit can be connected to and disconnected from the upper limb unit, the fitting belt, and the lower limb unit.

In a body fat measurement device according to one or more embodiments of the present invention, the lower limb unit includes a body weight measurement unit that measures the weight of the measurement subject.

According to one or more embodiments of the present invention, a body fat measurement device capable of measuring a body fat mass such as a visceral fat mass easily and accurately in a household or the like can be achieved.

DETAILED DESCRIPTION OF INVENTION

Figure 1:
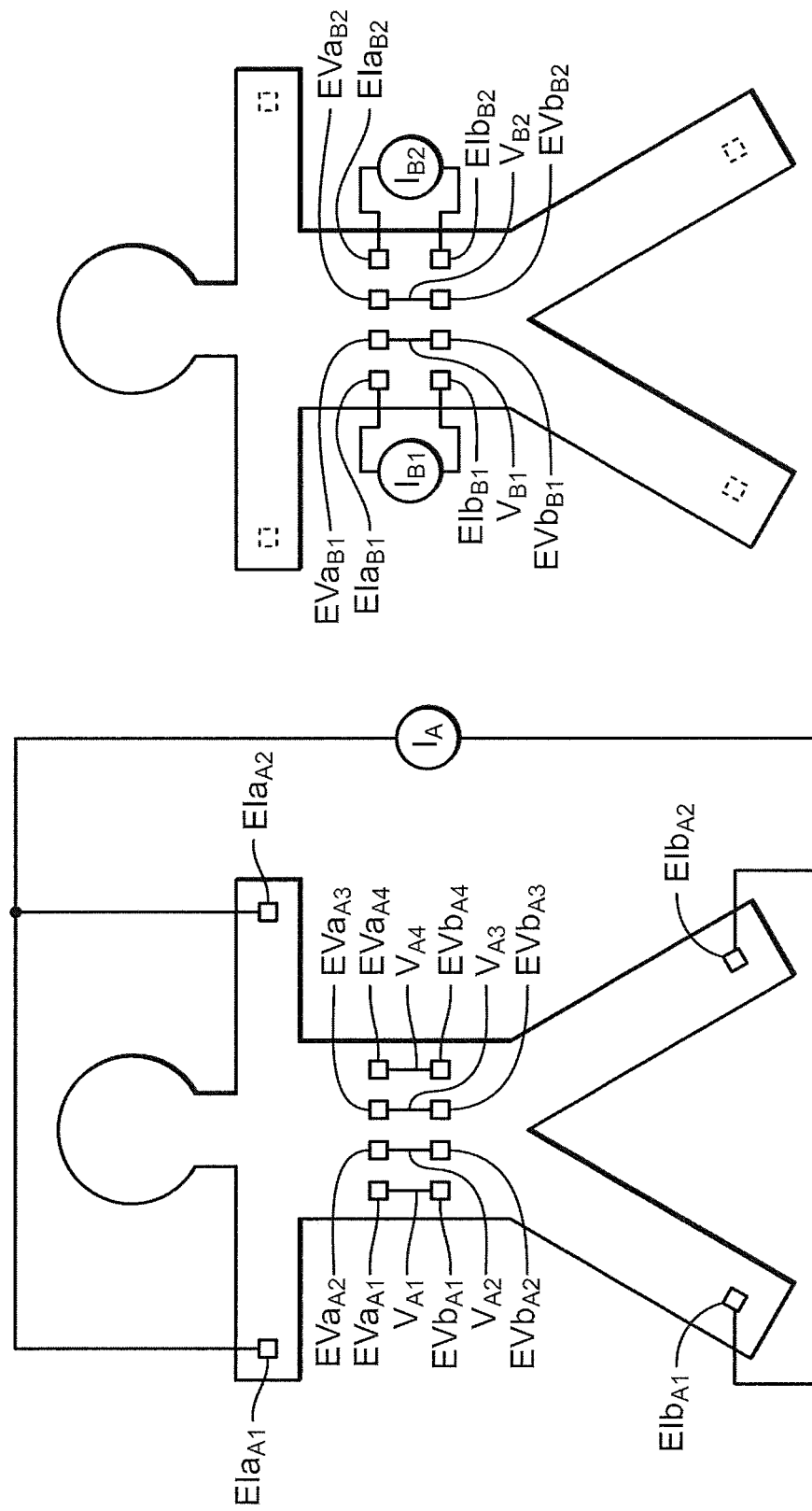
FIG. 1A is a diagram illustrating fundamentals of measurement performed by a body fat measurement device according to a first embodiment, and illustrates the placement of electrodes when obtaining a body impedance for the entire trunk area.
FIG. 1B is also a diagram illustrating fundamentals of measurement performed by the body fat measurement device according to the first embodiment, and illustrates the placement of electrodes when obtaining a body impedance for a surface layer area on the back area side of the trunk area.

Body fat measurement devices according to one or more embodiments of the present invention will be described in detail hereinafter with reference to the drawings. When numbers, amounts, and so on are discussed in the following embodiments, unless explicitly mentioned otherwise, the scope of the present invention is not necessarily limited to those numbers, amounts, and so on. In the embodiments, identical and corresponding components may be assigned identical reference numerals, and redundant descriptions thereof may be omitted.

Before describing the various embodiments of the present invention, definitions will be given for terms expressing parts of the body. "Trunk area" refers to the area excluding the head, neck, and four limbs, and corresponds to the trunk of the body. "Back area" refers to the area located on the back side of the stated trunk area, and corresponds to the area of the stated trunk area excluding the abdominal area side and the chest area side. "Back area surface" refers to the entire body surface of the back area, and indicates the surface of the trunk area that can be seen when a measurement subject is observed from the back side. Finally, "body axis" refers to an axis located along the direction in which the trunk area extends, or in other words, an axis extending in a direction approximately perpendicular to a side cross-section of the measurement subject's trunk area.

First Embodiment

Fundamentals of Measurement Performed by Body Fat Measurement Device 1A

The fundamentals of measurement performed by a body fat measurement device 1A (see FIG. 3) according to the present embodiment will be described with reference to FIGS. 1A and 1B. FIG. 1A is a diagram illustrating the placement of electrodes when obtaining a body impedance for the entire trunk area. FIG. 1B, meanwhile, is a diagram illustrating the placement of electrodes when obtaining a body impedance for a surface layer area on the back area side of the trunk area. FIGS. 1A and 1B both illustrate the measurement subject from the back side thereof As shown in FIG. 1A, electrodes $EIa_{A1}$ and $EIa_{A2}$ are attached to the surface of the left hand of the measurement subject and the surface of the right hand of the measurement subject, respectively. Likewise, electrodes $EIb_{A1}$ and $EIb_{A2}$ are attached to the surface of the left foot of the measurement subject and the surface of the right foot of the measurement subject, respectively. Four pairs of electrodes are attached to the back area surface of the measurement subject, with each pair disposed so as to follow the body axis direction, and with the four pairs arranged in the widthwise direction of the trunk area. Thus a total of eight electrodes, or electrodes $EVa_{A1}$, $EVb_{A1}$, $EVa_{A2}$, $EVb_{A2}$, $EVa_{A3}$, $EVb_{A3}$, $EVa_{A4}$, and $EVb_{A4}$, are attached to the back area surface of the measurement subject.

A constant current $I_A$ that passes through the trunk area is applied to the measurement subject using the electrodes $EIa_{A1}$, $EIa_{A2}$, $EIb_{A1}$, and $EIb_{A2}$. A potential difference $V_{A1}$ is detected using the electrodes $EVa_{A1}$ and $EVb_{A1}$, a potential difference $V_{A2}$ is detected using the electrodes $EVa_{A2}$ and $EVb_{A2}$, a potential difference $V_{A3}$ is detected using the electrodes $EVa_{A3}$ and $EVb_{A3}$, and a potential difference $V_{A4}$ is detected using the electrodes $EVa_{A4}$ and $EVb_{A4}$.

A body impedance Zt of the entire trunk area is calculated from the potential differences $V_{A1}$, $V_{A2}$, $V_{A3}$, and $V_{A4}$. According to one or more embodiments of the present invention, the body impedance Zt is calculated based on the average value of the potential differences $V_{A1}$, $V_{A2}$, $V_{A3}$, and $V_{A4}$. Doing so makes it possible to reduce the influence of variations in the fat distribution within the trunk area.

The constant current $I_A$ flows between both hands and both feet, which are located at a distance from the trunk area. Almost all of the constant current $I_A$ passes through an area of low electrical resistance (that is, areas aside from fat). The stated body impedance Zt calculated from the potential differences $V_{A1}$, $V_{A2}$, $V_{A3}$, and $V_{A4}$ measured using the constant current $I_A$ is greatly influenced by the amount of non-fat areas (internal organs, muscle, and bone) within the trunk area. Accordingly, the area occupied by non-fat areas (called a "non-fat cross-sectional area" hereinafter) Sa in the cross-section of the trunk area in an area corresponding to the location of the navel can be estimated based on the stated body impedance Zt.

Meanwhile, as shown in FIG. 1B, four pairs of electrodes are attached to the back area surface of the measurement subject, with each pair disposed so as to follow the body axis direction, and with the four pairs arranged in the widthwise direction of the trunk area. Thus a total of eight electrodes, or electrodes $EIa_{B1}$, $EIb_{B1}$, $EVa_{B1}$, $EVb_{B1}$, $EVa_{B2}$, $EVb_{B2}$, $EIa_{B2}$, and $EIb_{B2}$, are attached to the back area surface of the measurement subject.

A constant current $I_{B1}$ that passes through the back area locally is applied to the measurement subject using the electrodes $EIa_{B1}$ and $EIb_{B1}$, and a constant current $I_{B2}$ that passes through the back area locally is applied to the measurement subject using the electrodes $EIa_{B2}$ and $EIb_{B2}$. The current values of the constant currents $I_{B1}$ and $I_{B2}$ are set to the same value. While the constant currents $I_{B1}$ and $I_{B2}$ are applied, a potential difference $V_{B1}$ is detected using the electrodes $EVa_{B1}$ and $EVb_{B1}$, and a potential difference $V_{B2}$ is detected using the electrodes $EVa_{B2}$ and $EVb_{B2}$ attached to the back area surface.

A body impedance Zs of the surface layer area on the back area side of the trunk area is calculated form the potential differences $V_{B1}$ and $V_{B2}$. According to one or more embodiments of the present invention, the body impedance Zs is calculated based on the average value of the potential differences $V_{B1}$ and $V_{B2}$. Doing so makes it possible to reduce the influence of variations in the fat distribution and the like in the surface layer area in the back area of the trunk area. Potential differences can also be measured in four locations by switching circuits so that the electrodes to which the current was applied serve as electrodes for detecting the potential differences and the electrodes that were detecting the potential differences serve as electrodes for current application. Doing so makes it possible to further reduce the influence of variations in the subcutaneous fat and so on.

In this state, the constant currents $I_{B1}$ and $I_{B2}$ are applied locally to the back area of the trunk area. Thus, almost all of both the applied constant currents $I_{B1}$ and $I_{B2}$ pass through the surface layer area of the back area. The stated body impedance Zs calculated from the potential differences $V_{B1}$ and $V_{B2}$ measured using the constant currents $I_{B1}$ and $I_{B2}$ is greatly influenced by the subcutaneous fat mass. Accordingly, the subcutaneous fat cross-sectional area (called a "subcutaneous fat cross-sectional area" hereinafter) Sb in the cross-section of the trunk area including the location of the navel can be estimated based on the stated body impedance Zs.

Next, an example of a computation process for calculating a visceral fat mass using the stated body impedances Zt and Zs will be described.

If the overall area of the cross-section of the trunk area at the area corresponding to the location of the navel (called a "trunk area cross-sectional area" hereinafter) is taken as St, a visceral fat cross-sectional area Sx can be calculated through the following Formula (1) using the trunk area cross-sectional area St, the non-fat cross-sectional area Sa, and the subcutaneous fat cross-sectional area Sb.

$$Sx = St - Sa - Sb \qquad \text{Formula (1)}$$

The trunk area cross-sectional area St can be calculated using the circumferential length of the trunk area (the so-called waist length), the width of the trunk area, the depth of the trunk area, and so on. For example, when calculating the trunk area cross-sectional area St from the trunk area circumferential length, when the trunk area circumferential length is taken as t, the trunk area cross-sectional area St can be approximated from the following Formula (2).

$$St = t^2/(4 \times \pi) \quad \text{Formula (2)}$$

The trunk area cross-sectional area St approximated through the stated Formula (2) is highly likely to contain a significant degree of error. Thus, according to one or more embodiments of the present invention, a more accurate trunk area cross-sectional area St is found by multiplying that trunk area cross-sectional area St by a coefficient a for reducing error. This coefficient a is obtained, for example, by finding the optimum value for a that fulfills $St' = \alpha \times t^2/(4 \times \pi)$, from the relationship between the stated t and a trunk area cross-sectional area St' obtained from a sample of a large number of X-ray CT images.

Accordingly, the stated Formula (2) can approximate with a lower degree of error through the following Formula (3) by using the coefficient a.

$$St = \alpha \times t^2/(4 \times \pi) \quad \text{Formula (3)}$$

According to one or more embodiments of the present invention, the coefficient a multiplied for correction as described above is optimized as appropriate in accordance with information such as the measurement subject's sex, age, height, weight, and so on (hereinafter, this information will be referred to collectively as "measurement subject information"). The trunk area cross-sectional area St can be approximated with a higher degree of accuracy by changing the value of the stated coefficient a in accordance with the measurement subject information.

The non-fat cross-sectional area Sa can be calculated based on the body impedance Zt of the entire trunk area. However, the non-fat cross-sectional area Sa cannot be accurately calculated using only the body impedance Zt of the entire trunk area. The non-fat cross-sectional area Sa tends to be proportional to the size of the trunk area, and thus it is necessary to further convert the value obtained from the body impedance Zt in order to calculate the non-fat cross-sectional area Sa. Accordingly, the non-fat cross-sectional area Sa can be expressed through, for example, the following Formula (4).

$$Sa = \beta \times t \times (1/Zt) \quad \text{Formula (4)}$$

The stated t is the value of the trunk area circumferential length, as mentioned above, and is thus a value that is related to the size of the trunk area. The value related to the size of the trunk area is not limited to the stated t, and, for example, the trunk area cross-sectional area St may be used, or the width or depth of the trunk area may be used.

The stated β represents a coefficient for converting the body impedance Zt of the entire trunk area into the non-fat cross-sectional area Sa, and an optimum value can be found, for example, based on a sample of a large number of X-ray CT images, in the same manner as when finding the coefficient α. The optimum value for β that fulfils $Sa' = \beta \times t \times (1/Zt)$ can be found from the relationship between a non-fat cross-sectional area Sa' obtained from a sample of a large number of X-ray CT images, the body impedance Zt of the entire trunk area of the measurement subject imaged by the X-ray CT, and the stated t.

According to one or more embodiments of the present invention, the stated coefficient β is optimized as appropriate in accordance with the measurement subject information, in the same manner as the coefficient a mentioned above. The non-fat cross-sectional area Sa can be approximated with a higher degree of accuracy by changing the value of the stated coefficient β in accordance with the measurement subject information.

The subcutaneous fat cross-sectional area Sb can be calculated based on the body impedance Zs of the surface layer area on the back area side of the trunk area. However, the subcutaneous fat cross-sectional area Sb cannot be accurately calculated using only the body impedance Zs of the surface layer area on the back area side of the trunk area. The subcutaneous fat cross-sectional area Sb tends to be proportional to the size of the trunk area, and thus, it is necessary to further convert the value obtained from the body impedance Zs in order to calculate the subcutaneous fat cross-sectional area Sb. Accordingly, the subcutaneous fat cross-sectional area Sb can be expressed through, for example, the following Formula (5).

$$Sb = \gamma \times t \times Zs \quad \text{Formula (5)}$$

The stated t is the value of the trunk area circumferential length, as mentioned above, and is thus a value that is related to the size of the trunk area. The value related to the size of the trunk area is not limited to the stated t, and, for example, the trunk area cross-sectional area St may be used, or the width or depth of the trunk area may be used.

The stated coefficient γ is a coefficient for converting the body impedance Zs of the surface layer area on the back area side of the trunk area into the subcutaneous fat cross-sectional area Sb, and an optimum value can be found, for example, based on a sample of a large number of X-ray CT images, in the same manner as when finding the coefficient a or the coefficient β. The optimum value for γ that fulfils $Sb' = \gamma \times t \times Zs$ can be found from the relationship between a subcutaneous fat cross-sectional area Sb' obtained from a sample of a large number of X-ray CT images, the body impedance Zs of the surface layer area on the back area side of the trunk area of the measurement subject imaged by the X-ray CT, and the stated t.

According to one or more embodiments of the present invention, the stated coefficient γ is optimized as appropriate in accordance with the measurement subject information, in the same manner as the coefficient α and the coefficient β mentioned above. The subcutaneous fat cross-sectional area Sb can be approximated with a higher degree of accuracy by changing the value of the stated coefficient γ in accordance with the measurement subject information.

As described thus far, in the body fat measurement device according to the present embodiment, the visceral fat cross-sectional area Sx is calculated based on the stated Formula (1) using the trunk area cross-sectional area St, the non-fat cross-sectional area Sa calculated based on the body impedance Zt of the entire trunk area, and the subcutaneous fat cross-sectional area Sb calculated based on the body impedance Zs of the surface layer area on the back area side of the trunk area. The visceral fat cross-sectional area Sx is calculated based on the following Formula (6) by substituting the stated Formula (3) through Formula (5) in the stated Formula (1).

$$Sx = \alpha \times t^2/(4 \times \pi) - \beta \times t \times (1/Zt) - \gamma \times t \times Zs \quad \text{Formula (6)}$$

Functional Blocks of Body Fat Measurement Device 1A

Figure 2:
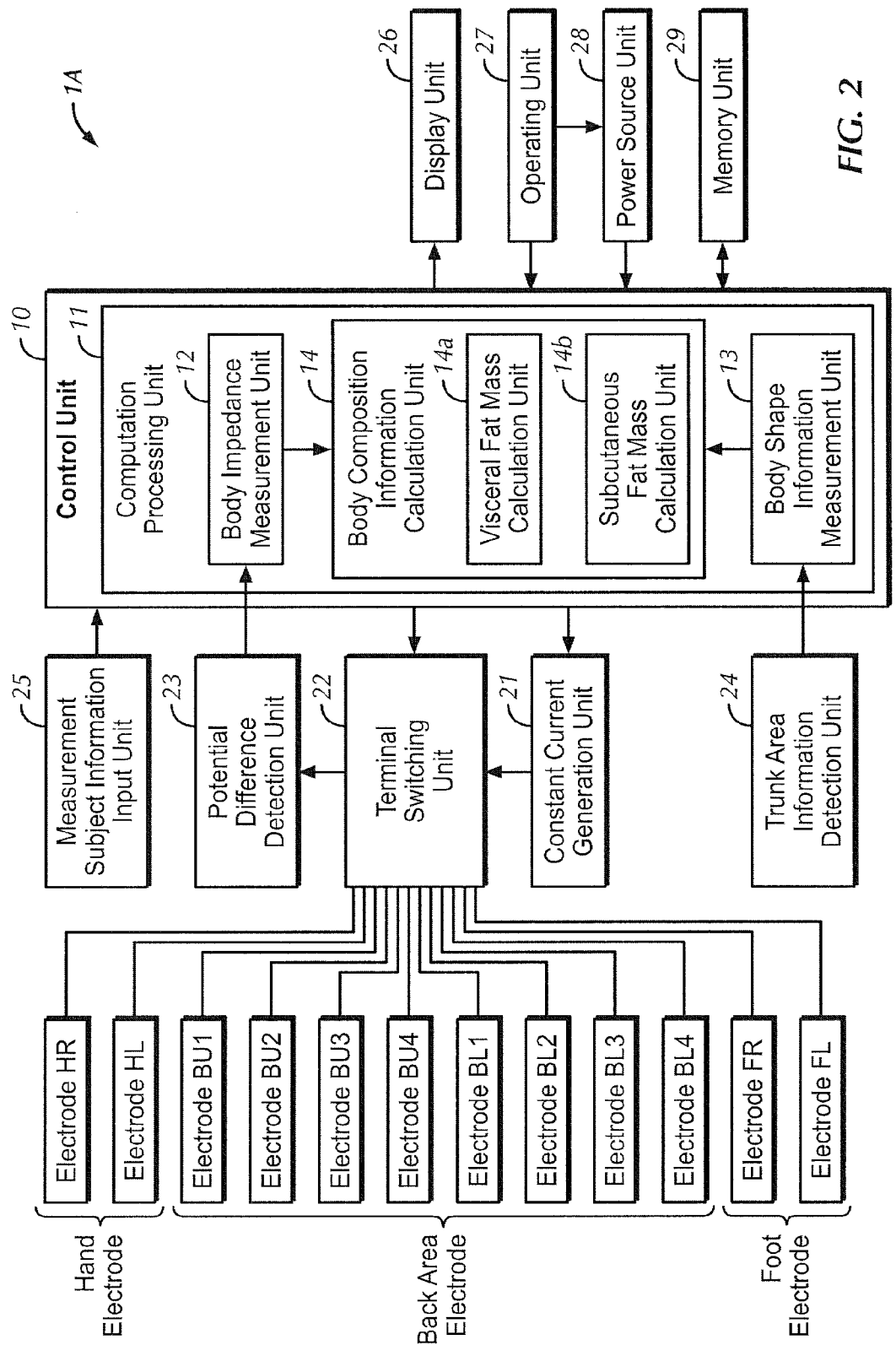
FIG. 2 is a diagram illustrating the functional block configuration of the body fat measurement device according to the first embodiment.

FIG. 2 is a diagram illustrating the functional block configuration of the body fat measurement device 1A according to the present embodiment. As shown in FIG. 2, the body fat measurement device 1A primarily includes a control unit 10, a constant current generation unit 21, a terminal switching unit 22, a potential difference detection unit 23, a trunk area information detection unit 24, a measurement subject information input unit 25, a display unit 26, an operating unit 27, a power source unit 28, a memory unit 29, and multiple electrodes HR, HL, BU1-BU4, BL1-BL4, FR, FL that are affixed to the measurement subject's body.

The control unit 10 controls a computation processing unit 11. The computation processing unit 11 includes a body impedance measurement unit 12, a body shape information measurement unit 13, and a body composition information calculation unit 14. The control unit 10 is configured of, for example, a CPU (Central Processing Unit), and controls the body fat measurement device 1A as a whole. The control unit 10 outputs instructions to the various aforementioned functional blocks, accepts inputs of various types of information from the various functional blocks, performs various types of computation processes based on various types of information, and so on. The various types of computation processes are carried out by the computation processing unit 11.

The aforementioned multiple electrodes include: hand electrodes HR and HL serving as upper limb electrodes placed in contact with surfaces of the upper limbs of the measurement subject; back area electrodes BU1-BU4 and BL1-BL4 placed in contact with the back area surface of the measurement subject; and foot electrodes FR and FL serving as lower limb electrodes placed in contact with surfaces of the lower limbs of the measurement subject.

The hand electrodes HR and HL are placed in contact with the measurement subject's palms, whereas the foot electrodes FR and FL are placed in contact with the soles of the measurement subject's feet. As shown in FIGS. 1A and 1B, the back area electrodes BU1-BU4 and BL1-BL4 are arranged in rows and placed in contact with the back area surface of the measurement subject. The hand electrodes FIR and HL, back area electrodes BU1-BU4 and BL1-BL4, and foot electrodes FR and FL are all electrically connected to the aforementioned terminal switching unit 22.

The terminal switching unit 22 is configured of, for example, a relay circuit; based on instructions inputted from the control unit 10, the terminal switching unit 22 electrically connects specific electrodes selected from the stated multiple electrodes to the constant current generation unit 21 and electrically connects specific electrodes selected from the stated multiple electrodes to the potential difference detection unit 23. The electrodes electrically connected to the constant current generation unit 21 by the terminal switching unit 22 function as constant current application electrodes, and the electrodes electrically connected to the potential difference detection unit 23 by the terminal switching unit 22 function as potential difference detection electrodes.

By the terminal switching unit 22 operating based on instructions inputted from the control unit 10, the respective multiple electrodes HR, HL, BU1-BU4, BL1-BL4, FR, FL function as the respective electrodes $EIa_{A1}$, $EIa_{A2}$, $EIb_{A1}$, $EIb_{A2}$, $EVa_{A1}$, $EVb_{A1}$, $EVa_{A2}$, $EVb_{A2}$, $EVa_{A3}$, $EVb_{A3}$, $EVa_{A4}$, and $EVb_{A4}$ shown in FIG. 1A and the respective electrodes $EIa_{A1}$, $EIb_{A1}$, $EVa_{B1}$, $EVb_{B1}$, $EIa_{B2}$, $EIb_{B2}$, $EVa_{B2}$, and $EVb_{B2}$ shown in FIG 1B.

The constant current generation unit 21 generates a constant current based on an instruction inputted from the control unit 10. The constant current is supplied to the aforementioned constant current application electrodes through the terminal switching unit 22. A high-frequency current (for example, 50 kHz, 500 μA) that can be used effectively for measuring body composition information is selected as the constant current. The constant current is applied to the measurement subject through the constant current application electrodes.

The potential difference detection unit 23 detects a potential difference between the electrodes electrically connected to the potential difference detection unit 23 by the terminal switching unit 22 (that is, the potential difference detection electrodes). The detected potential difference is outputted to the control unit 10. The potential difference between the potential difference detection electrodes is detected in a state in which the constant current is applied to the measurement subject.

The trunk area information detection unit 24 is configured of, for example, an electronic tape or the like, and measures the circumferential length of the measurement subject's trunk area. The trunk area information detection unit 24 outputs a signal based on the value detected to the body shape information measurement unit 13.

The measurement subject information input unit 25 is configured of, for example, keys and the like that can be depressed by the measurement subject, and obtains the measurement subject information used in computation processes carried out by the computation processing unit 11. The measurement subject information input unit 25 accepts the input of the measurement subject information, and then outputs the measurement subject information to the control unit 10.

The measurement subject information input unit 25 is not absolutely necessary in the configuration according to one or more embodiments of the present invention. Whether or not to provide the measurement subject information input unit 25 can be determined based on whether or not it is necessary to use the measurement subject information in the computation processes performed by the computation processing unit 11. Rather than providing the trunk area information detection unit 24 and taking an actual measurement of the trunk area circumferential length, the configuration can also be such that the circumferential length, depth, width, or the like of the trunk area are inputted through the measurement subject information input unit 25 and computations are carried out by the computation processing unit using that information.

The computation processing unit 11 includes the body impedance measurement unit 12, the body shape information measurement unit 13, and the body composition information calculation unit 14. The body composition information obtainment unit 14 includes a visceral fat mass calculation unit 14a and a subcutaneous fat mass calculation unit 14b. The body impedance measurement unit 12 calculates the body impedance based on a signal inputted from the potential difference detection unit 23, and outputs that body impedance to the body composition information obtainment unit 14. The body shape information measurement unit 13 calculates the circumferential length of the measurement subject's trunk area based on a signal inputted from the trunk area information detection unit 24, and outputs that information to the body composition information calculation unit 14.

The body composition information obtainment unit 14 calculates and obtains the body composition information based on the body impedance inputted from the body impedance measurement unit 12, the circumferential length of the trunk area inputted from the body shape information measurement unit 13, and in some cases, the measurement subject information inputted from the measurement subject information input unit 25 as well. The visceral fat mass calculation unit 14a calculates a visceral fat mass and the subcutaneous fat mass calculation unit 14b calculates a subcutaneous fat mass.

The display unit 26 is configured of, for example, an LCD (Liquid Crystal Display) or the like, and displays the body composition information calculated by the body composition information obtainment unit 14. The visceral fat mass calculated by the visceral fat mass calculation unit 14a and the subcutaneous fat mass calculated by the subcutaneous fat mass calculation unit 14b are each displayed in the display unit 26 based on signals outputted from the control unit 10. With the body fat measurement device 1A, the visceral fat mass is displayed as, for example, the visceral fat cross-sectional area, and the subcutaneous fat mass is displayed as, for example, the subcutaneous fat cross-sectional area.

The operating unit 27 is configured of, for example, buttons and the like that can be depressed by the measurement subject, and is a unit through which commands are inputted to the body fat measurement device 1A by the measurement subject. The operating unit 27 includes various types of operation buttons such as a power button, a measure button, and so on. The power source unit 28 is an internal power source such as a battery, an external power source such as an AC outlet, or the like, and supplies electrical power to the control unit 10.

The memory unit 29 is configured of, for example, a RAM (random access memory) or a ROM (read-only memory), and stores various types of data, programs, and so on related to the body fat measurement device 1A. The memory unit 29 stores, for example, the measurement subject information, the calculated body composition information, a body composition information measurement program for executing a body composition information measurement process (mentioned later with reference to FIG. 7), and so on.

Structure of Body Fat Measurement Device 1A

Figure 3:
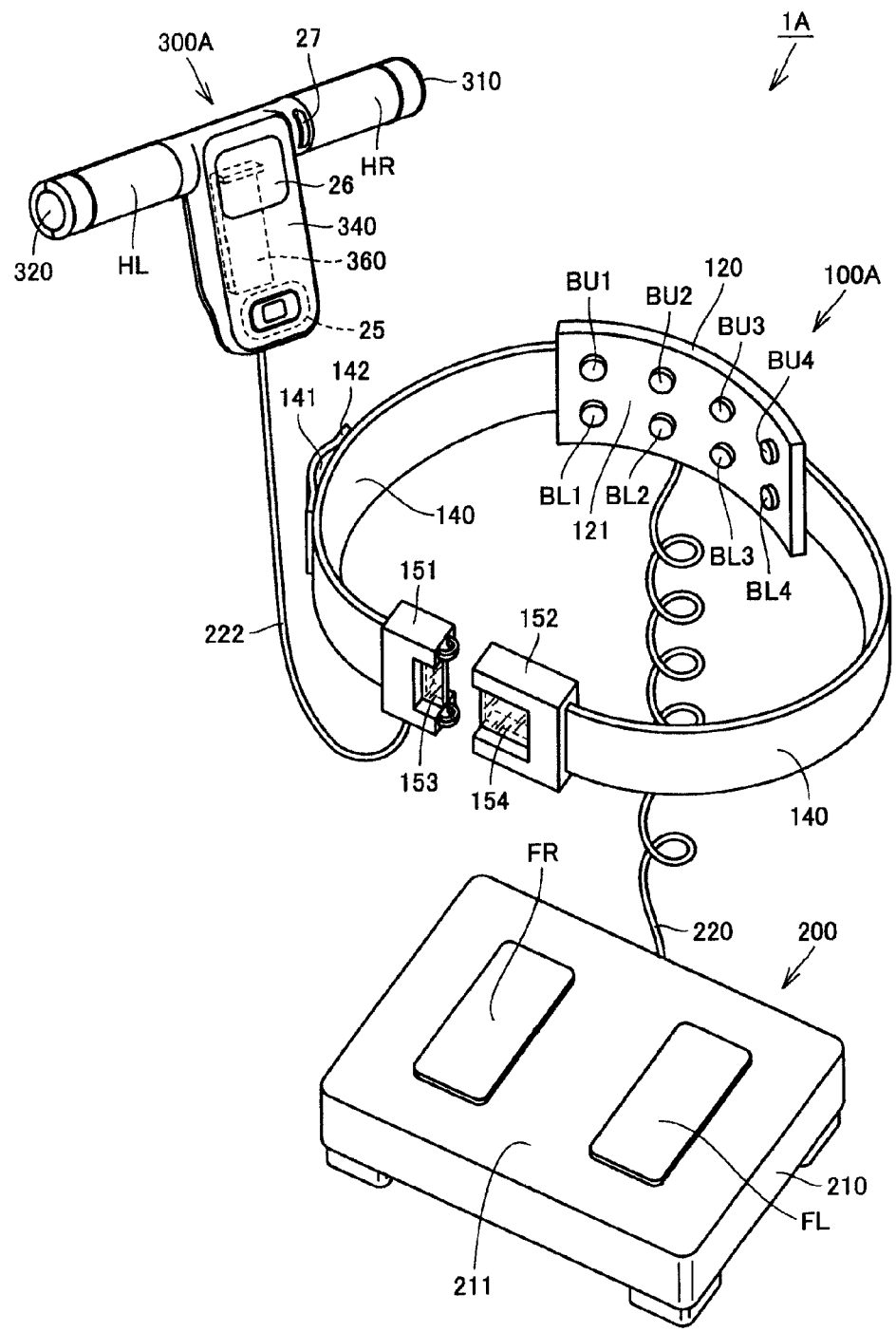
FIG. 3 is a perspective view illustrating the body fat measurement device according to the first embodiment.

FIG. 3 is a perspective view illustrating the body fat measurement device 1A according to the present embodiment. The body fat measurement device 1A includes a fitting belt 100A, an upper limb unit 300A, and a lower limb unit 200.

The fitting belt 100A has a band-shaped belt portion 140, buckle portions 151 and 152 that can engage with each other, and an electrode support member 120, having a curved plate shape, attached to a rear area of the belt portion 140. The belt portion 140 is capable of surrounding the measurement subject's trunk area. An electronic tape or the like (not shown), serving as a trunk area information detection unit, is provided in the belt portion 140 along the lengthwise direction thereof.

A band-shaped member 142 serving as a first engagement member is stitched to the outside surface of the belt portion 140, and an opening 141 is formed as a result of the stitching. The band-shaped member 142 may be attached at any desired position in the lengthwise direction of the belt portion 140.

The buckle portion 151 is attached to one end of the belt portion 140 (the right hand side), whereas the buckle portion 152 is attached to the other end of the belt portion 140 (the left hand side). According to one or more embodiments of the present invention, the belt portion 140 is configured so that when the buckle portions 151 and 152 are engaged with each other, the length in the lengthwise direction can be adjusted automatically or manually. This adjustment makes it possible to tighten the belt portion 140 around the measurement subject's trunk area after the buckle portions 151 and 152 have been engaged with each other. Using the trunk area information detection unit configured of the electronic tape or the like, the fitting belt 100A measures the circumferential length of the measurement subject's trunk area after the belt portion 140 has been tightened around the measurement subject's trunk area.

The buckle portion 151 has a light-transmissive window portion 153, and the buckle portion 152 has a light-transmissive window portion 154. After the belt portion 140 has been tightened around the measurement subject's trunk area, the area of the measurement subject's navel can be visually confirmed from outside the belt portion 140 through the light-transmissive window portions 153 and 154. A predetermined marker (not shown) is added to the surface of the light-transmissive window portions 153 and 154. The belt portion 140 is designed to be tightened on the measurement subject when positioned so that the marker and the location of the measurement subject's navel match.

The electrode support member 120 is configured of a curved plate that is bent so that both ends thereof are positioned forward and the center thereof is positioned rearward. The aforementioned back area electrodes BU1-BU4 and BL1-BL4 are provided so as to be exposed on a front surface 121 of the electrode support member 120. According to one or more embodiments of the present invention, the back area electrodes BU1-BU4 and BL1-BL4 protrude slightly from the front surface 121 of the electrode support member 120.

The electrode support member 120 is positioned and attached on the inner surface of the belt portion 140 so that surfaces of the back area electrodes BU1-BU4 and BL1-BL4 that make contact with the back area surface of the measurement subject face forward. By being tightened around the measurement subject's trunk area, the belt portion 140 brings the back area electrodes BU1-BU4 and BL1-BL4 into contact with the back area surface of the measurement subject in a pressurized state.

Figure 4A:
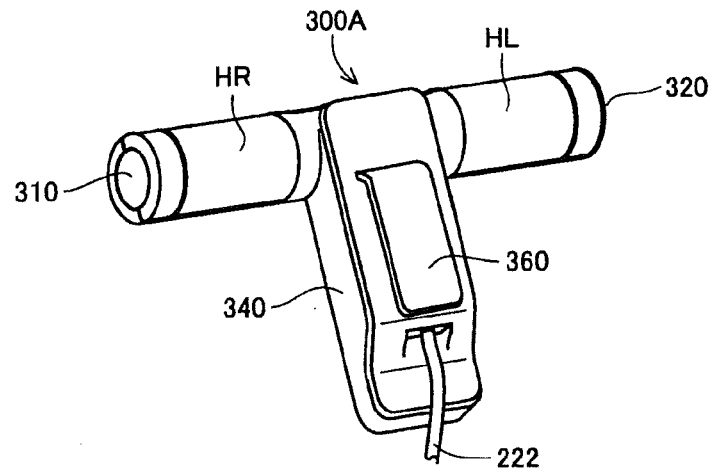
FIG. 4A is a perspective view illustrating an upper limb unit according to the first embodiment from the rear side.

FIG. 4A is a perspective view illustrating a rear surface side of the upper limb unit 300A. As shown in FIGS. 3 and 4A, the upper limb unit 300A has an overall T shape, and is configured of a box-shaped main body unit 340, a right-hand grip portion 310 serving as a gripping portion that is gripped by the measurement subject's right hand, and a left-hand grip portion 320 serving as a gripping portion that is gripped by the measurement subject's left hand.

The hand electrode HR is provided in an exposed state on the right-hand grip portion 310. The hand electrode HL is provided in an exposed state on the left-hand grip portion 320. An inverted L-shape hanging member 360 serving as a second engagement member is provided on the rear surface of the main body unit 340 so as to project downward. The hanging member 360 has a plate shape that can be inserted into the aforementioned opening 141. The shape of the hanging member 360 is, however, not limited to a plate shape, and may be any shape, such as a rod shape, having a predetermined length that enables the hanging member 360 to be inserted into the aforementioned opening 141.

Figure 4B:
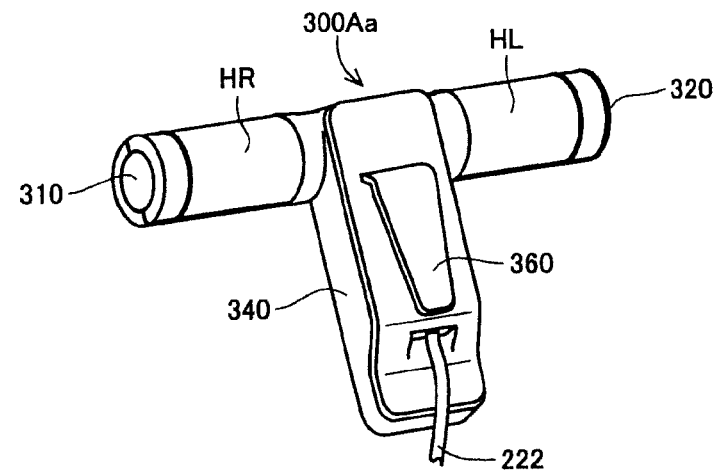
FIG. 4B is a perspective view illustrating another example of the upper limb unit according to the first embodiment from the rear side.

As another example, in the case where the hanging member 360 is configured in a plate shape, according to one or more embodiments of the present invention, the leading end side of the hanging member 360 (that is, the side that is inserted into the opening 141) has a tapered shape, as with an upper limb unit 300Aa shown in FIG. 4B. The upper limb unit 300Aa is easy to insert into and remove from the fitting belt 100A.

Figure 4C:
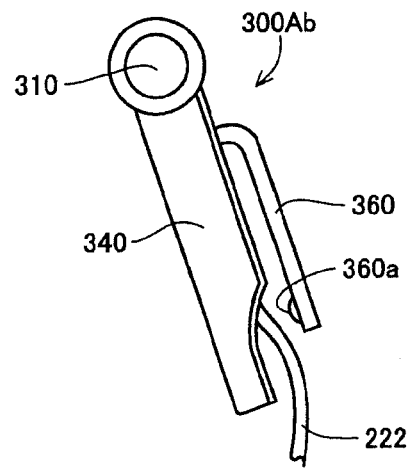
FIG. 4C is a side view illustrating yet another example of the upper limb unit according to the first embodiment.

As yet another example, in the case where the hanging member 360 is configured in a plate shape, a projection 360a may be provided in the leading end side of the hanging member 360 (that is, the side that is inserted into the opening 141), as with an upper limb unit 300Ab shown in FIG. 4C. The projection 360a can suppress the upper limb unit 300Ab from falling when the upper limb unit 300Ab is attached to the fitting belt 100A.

The measurement subject information input unit 25, the display unit 26, and the operating unit 27 are each provided in respective positions in the front surface side of the main body unit 340 (see FIG. 3). The display unit 26 displays the body composition information calculated by the body composition information obtainment unit 14 (see FIG. 2). According to one or more embodiments of the present invention, the operating unit 27, which is used for accepting instructions from the measurement subject, is provided so as to include a location that is adjacent to the hand electrode RR, as shown in FIG. 3. Doing so makes it unnecessary for the measurement subject to move his/her fingers during measurement, which improves the operability.

The lower limb unit 200 is configured of a box-shaped platform portion 210. The aforementioned foot electrodes FR and FL are respectively provided in predetermined locations of a top surface 211 of the platform portion 210 in an exposed state. The measurement subject can step onto the top surface 211.

The lower limb unit 200 may include a body weight measurement function. By providing a load cell or the like that serves as a body weight measurement unit for detecting a load on the lower limb unit 200, the weight of the measurement subject standing on the lower limb unit 200 can be measured by the body weight measurement unit. If the configuration is such that body weight information measured by the body weight measurement unit provided in the lower limb unit 200 is inputted into the control unit 10, the actual measured body weight of the measurement subject can be used as measurement subject information in the various types of computation processes.

One end of a connection cable 220 is connected to the lower limb unit 200. The other end of the connection cable 220 is connected to the back area electrodes BU1-BU4 and BL1-BL4 of the fitting belt 100A.

One end of a connection cable 222 is connected to the upper limb unit 300A. The other end of the connection cable 222 is connected to the buckle portion 151 of the fitting belt 100A. The other end of the connection cable 222 is electrically connected to the back area electrodes BU1-BU4 and BL1-BL4 by another connection cable (not shown) installed within the belt portion 140 and extending from the buckle portion 151. As a result, the upper limb unit 300A, the back area electrodes BU1-BU4 and BL1-BL4 in the fitting belt 100A, and the lower limb unit 200 have a hard-wired electrical connection.

The connection cable 220 may be configured so as to be taken up into a reel member (not shown) provided in the lower limb unit 200. The connection cable 222 may also be configured so as to be taken up into a reel member (not shown) provided in the buckle portion 151.

The control unit 10, the constant current generation unit 21, the terminal switching unit 22, the potential difference detection unit 23, the memory unit 29, and so on shown in FIG. 2 may be provided within the lower limb unit 200, or may be provided within the upper limb unit 300A. The measurement subject information input unit 25, the display unit 26, and the operating unit 27 may be provided in the lower limb unit 200.

Fitting of Fitting Belt 100A onto Measurement Subject

Figure 5:
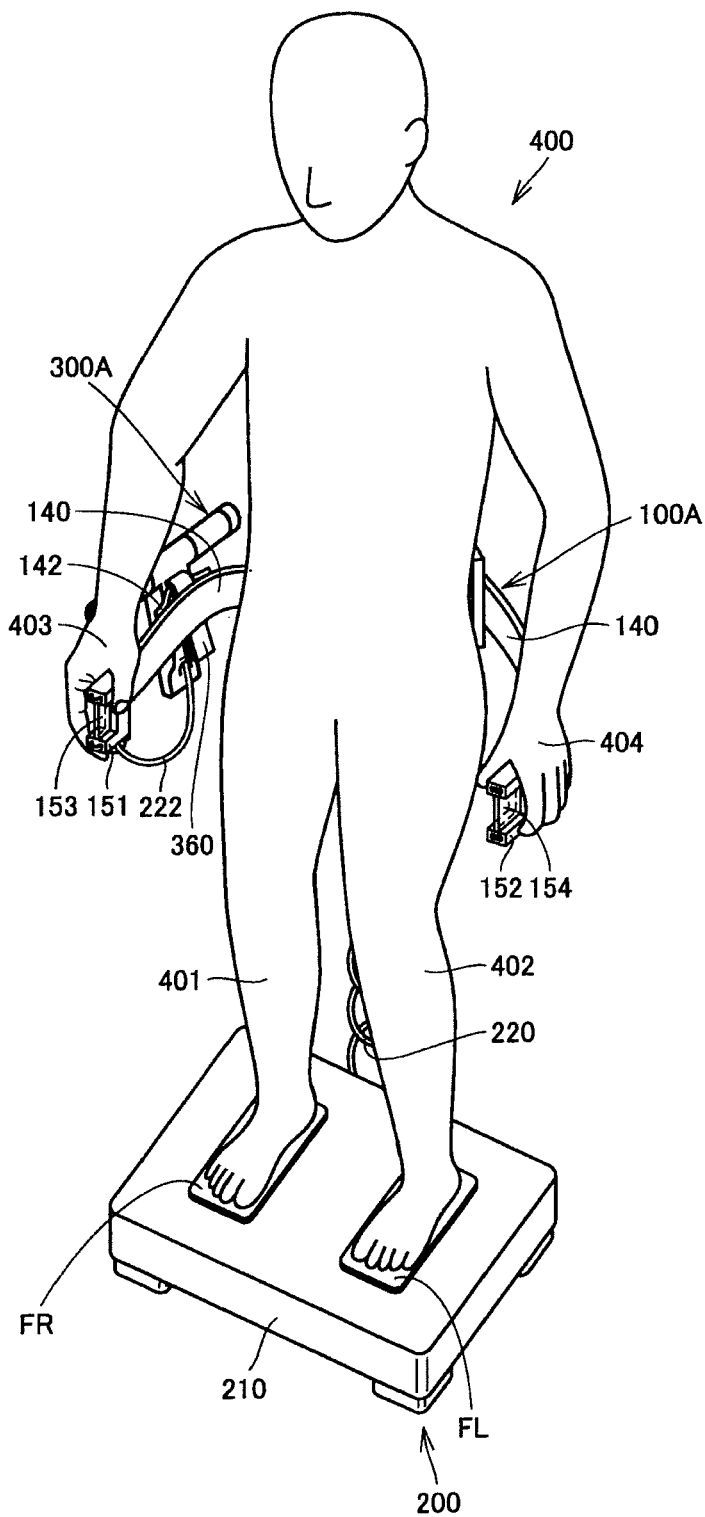
FIG. 5 is a diagram illustrating a state prior to a fitting belt of the body fat measurement device according to the first embodiment being fitted on a measurement subject.
Figure 6:
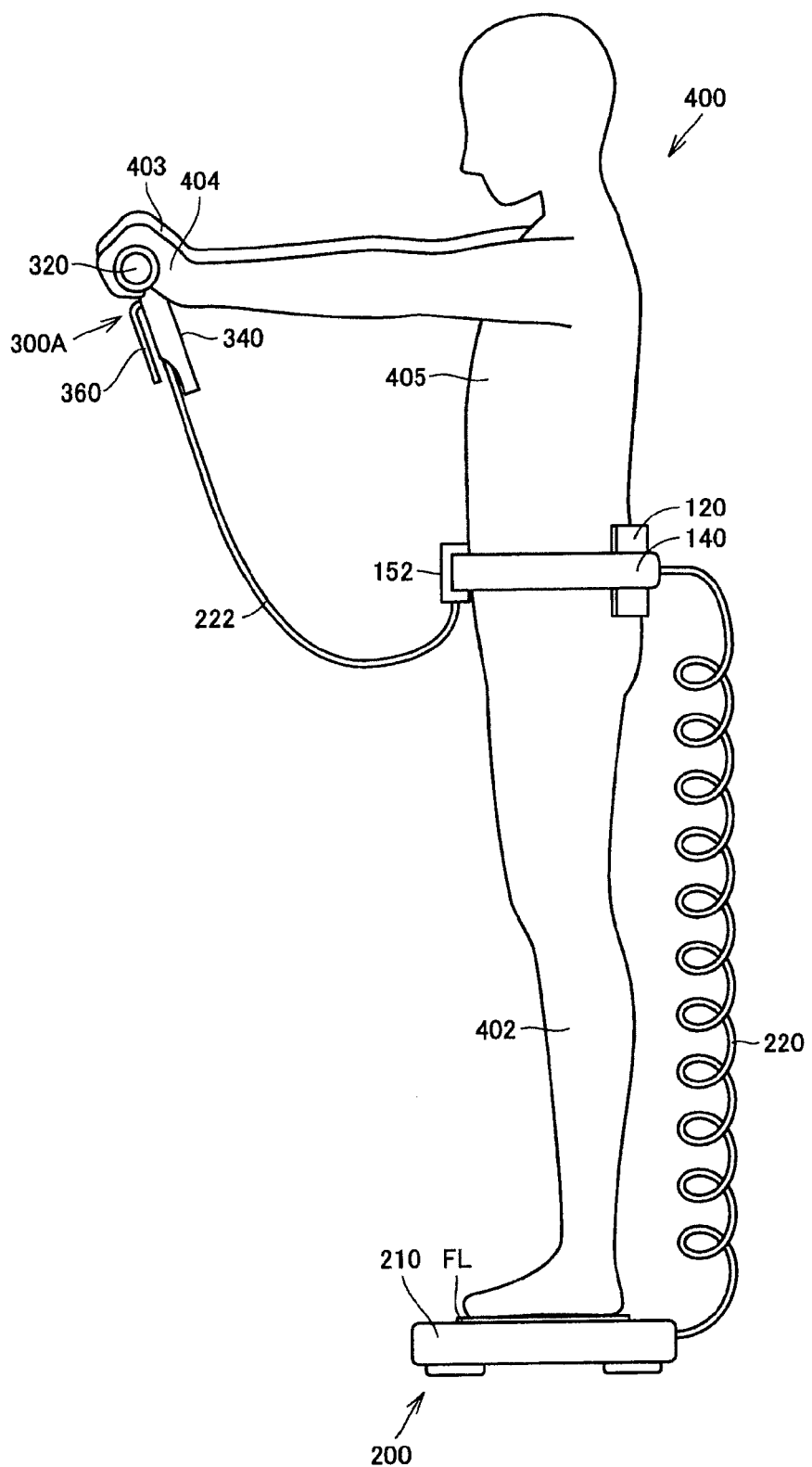
FIG. 6 is a diagram illustrating a state after the fitting belt of the body fat measurement device according to the first embodiment has been fitted on a measurement subject.

FIG. 5 illustrates a state prior to the fitting belt 100A being fitted onto the measurement subject. FIG. 6 illustrates a state after the fitting belt 100A has been fitted onto the measurement subject. A procedure to be carried out by the measurement subject when measuring a body fat mass or the like using the body fat measurement device 1A will be described with reference to FIG. 5 and FIG. 6.

As shown in FIG. 5, a measurement subject 400 first inserts the hanging member 360 of the upper limb unit 300A into the opening 141 in the fitting belt 100A. The upper limb unit 300A is attached to the fitting belt 100A by inserting the hanging member 360 into the opening 141.

The measurement subject 400 holds the fitting belt 100A to which the upper limb unit 300A is attached and steps onto the lower limb unit 200. The sole of a right foot 401 makes contact with the foot electrode FR, and the sole of a left foot 402 makes contact with the foot electrode FL.

The measurement subject 400 positions the fitting belt 100A so that the belt portion 140 surrounds his/her trunk area. The measurement subject 400 then engages the buckle portions 151 and 152 with each other. The measurement subject 400 adjusts the position of the belt portion 140 in the circumferential direction so that the predetermined marker (not shown) provided in the light-transmissive window portions 153 and 154 (see FIG. 3) matches the position of his/her navel. After engaging the buckle portions 151 and 152 with each other, the measurement subject 400 may step onto the lower limb unit 200 of the body fat measurement device 1A.

As shown in FIG. 6, the measurement subject 400 removes the upper limb unit 300A from the fitting belt 100A. The measurement subject 400 then presses the power button (not shown) at an appropriate timing. The measurement subject 400 grips the right-hand grip portion 310 (see FIG. 3) with the right hand 403 and grips the left-hand grip portion 320 (see FIG. 3) with the left hand 404. The palm of the right hand 403 makes contact with the hand electrode HR (see FIG. 3), whereas the palm of the left hand 404 makes contact with the hand electrode HL (see FIG. 3).

The measurement subject 400 then assumes a position in which the right hand 403 (right arm) and the left hand 404 (left arm) are at an approximately right angle to a trunk area 405. In the case where the reel member capable of taking up the connection cable 222 is provided in the buckle portion 151, the connection cable 222 is pulled out from the buckle portion 151 by the upper limb unit 300A being pulled in the forward direction.

The measurement subject 400 then manipulates the operating unit 27 (see FIG. 3) with the thumb of the right hand 403. In the case where the length of the belt portion 140 is adjusted automatically, the length of the belt portion 140 increases/decreases as necessary in response to the operating unit 27 being manipulated. However, in the case where the configuration is such that the length of the belt portion 140 is adjusted manually, according to one or more embodiments of the present invention, the measurement subject increases/decreases the length of the belt portion 140 as necessary at the stage of operations when the measurement subject matches the predetermined marker provided in the light-transmissive window portions 153 and 154 with the location of his/her navel.

After the belt portion 140 has been properly tightened around the measurement subject's trunk area, the trunk area circumferential length of the measurement subject 400 is measured by the trunk area information detection unit such as an electronic tape. However, the trunk area circumferential length may, as described above, be directly inputted by the measurement subject through the measurement subject information input unit 25.

Figure 7:
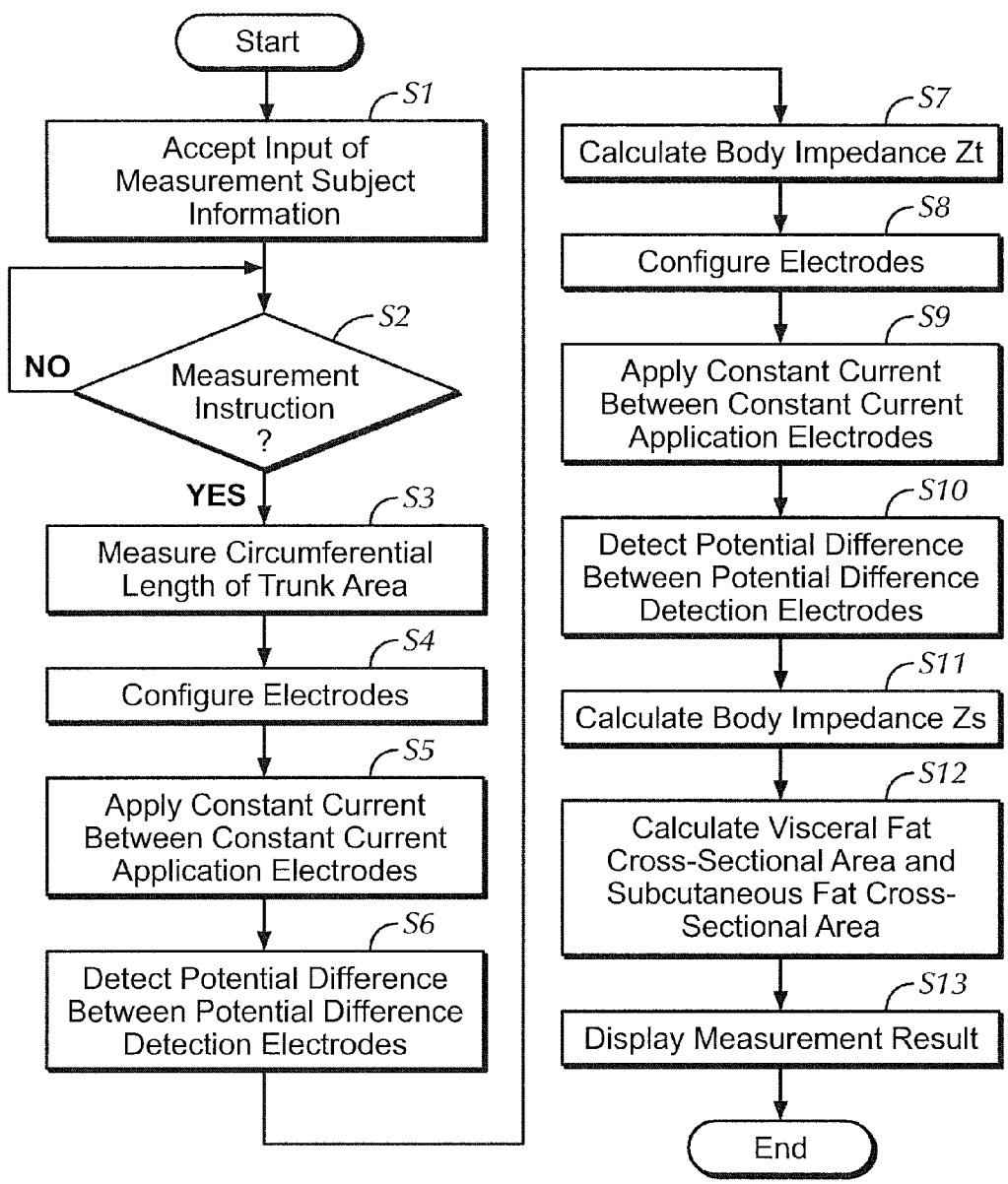
FIG. 7 is a flowchart illustrating a process performed by a control unit in the body fat measurement device according to the first embodiment.

FIG. 7 is a flowchart illustrating processing performed by the control unit 10 (see FIG. 2) of the body fat measurement device 1A. A series of processes executed by the control unit 10 will be described in order with reference to FIG. 2 and FIG. 7.

These processes are stored in advance in the memory unit 29 as a program. A visceral fat cross-sectional area measurement process, a subcutaneous fat cross-sectional area measurement process, and so on are realized by the control unit 10 when the control unit 10 including the computation processing unit 11 reads out and executes that program.

As shown in FIG. 7, the control unit 10 first accepts an input of the measurement subject information (step S1). The measurement subject information is temporarily saved in, for example, the memory unit 29. The control unit 10 then determines whether or not there has been an instruction to start the measurement (step S2). The control unit 10 stands by until there has been an instruction to start the measurement (NO in step S2), and advances to the next process in the case where an instruction to start the measurement has been detected (YES in step S2). The instruction to start the measurement is made by the measurement subject manipulating the operating unit 27.

The control unit 10 obtains the circumferential length of the measurement subject's trunk area based on a signal inputted from the trunk area information detection unit 24 (step S3). The trunk area circumferential length is temporarily saved in the memory unit 29. The control unit 10 outputs an instruction to the terminal switching unit 22 for switching the electrodes (step S4). The terminal switching unit 22 configures the multiple electrodes HR, HL, BU1-BU4, BL1-BL4, FR, and FL to the configuration of the electrodes shown in FIG. 1A.

The control unit 10 outputs an instruction to the constant current generation unit 21 for generating the constant current (step S5). The constant current generation unit 21 applies the generated constant current $I_A$ between the constant current application electrodes shown in FIG. 1A. The control unit 10 outputs an instruction to the potential difference detection unit 23 for detecting a potential difference (step S6). The potential difference detection unit 23 detects the potential differences $V_{A1}$, $V_{A2}$, $V_{A3}$, and $V_{A4}$ between the potential difference detection electrodes shown in FIG. 1A, and outputs the detected potential differences to the body impedance measurement unit 12.

The control unit 10 calculates the body impedance Zt using the body impedance measurement unit 12, based on the signal inputted from the potential difference detection unit 23 (step S7). The body impedance Zt is temporarily saved in the memory unit 29. The control unit 10 outputs an instruction to the terminal switching unit 22 for switching the electrodes (step S8). The terminal switching unit 22 configures the multiple electrodes HR, HL, BU1-BU4, BL1-BL4, FR, and FL to the configuration of the electrodes shown in FIG. 1B.

The control unit 10 outputs an instruction to the constant current generation unit 21 for generating the constant current (step S9). The constant current generation unit 21 applies the generated constant currents $I_{B1}$ and $I_{B2}$ between the constant current application electrodes shown in FIG. 1B. The control unit 10 outputs an instruction to the potential difference detection unit 23 for detecting a potential difference (step S10). The potential difference detection unit 23 detects the potential differences $V_{B1}$ and $V_{B2}$ between the potential difference detection electrodes shown in FIG. 1B, and outputs the detected potential differences to the body impedance measurement unit 12. The control unit 10 calculates the body impedance Zs using the body impedance measurement unit 12, based on the signal inputted from the potential difference detection unit 23 (step S11).

The body impedance Zs is temporarily saved in the memory unit 29. The control unit 10 calculates the visceral fat cross-sectional area Sx as the visceral fat mass using the visceral fat mass calculation unit 14a and calculates the subcutaneous fat cross-sectional area Sb as the subcutaneous fat mass using the subcutaneous fat mass calculation unit 14b, based on the trunk area circumferential length t detected in step S3, the body impedance Zt calculated in step S7, and the body impedance Zs calculated in step S11 (step S12). The calculated visceral fat cross-sectional area Sx and subcutaneous fat cross-sectional area Sb are temporarily saved in the memory unit 29.

The control unit 10 outputs, to the display unit 26, an instruction to display the visceral fat cross-sectional area Sx and subcutaneous fat cross-sectional area Sb (step S13). Based on this, the display unit 26 displays those measurement results. Through this, the body fat measurement device 1A completes the visceral fat cross-sectional area measurement process and the subcutaneous fat cross-sectional area measurement process. A typical value for the body impedance Zt is approximately 5 Ω, whereas atypical value for the body impedance Zs is approximately 80 Ω.

Actions and Effects

The upper limb unit 300A can be attached to the fitting belt 100A using the opening 141 provided in the fitting belt 100A and the hanging member 360 provided in the upper limb unit 300A. The measurement subject 400 holds the fitting belt 100A to which the upper limb unit 300A is attached and steps onto the lower limb unit 200. After the measurement subject 400 has fitted the fitting belt 100A around his/her trunk area, s/he can remove the upper limb unit 300A from the fitting belt 100A while remaining in an erect position.

According to the body fat measurement device 1A, the measurement subject 400 does not need to take actions such as picking up the upper limb unit 300A by squatting or bending over after fitting the fitting belt 100A around his/her trunk area. According to the body fat measurement device 1A, the measurement subject 400 can easily assume a position in preparation for measurement.

Because the measurement subject 400 does not need to squat or the like while wearing the fitting belt 100A, the fitting belt 100A does not shift from a desired position. According to the body fat measurement device 1A, body fat measurement can be easily and accurately carried out.

The back area electrodes BU1-BU4 and BL1-BL4 are provided in an exposed state on a rear area of the fitting belt 100A. The back area electrodes BU1-BU4 and BL1-BL4 can easily be brought into contact with the back area surface in a pressurized state by the measurement subject 400 wearing the fitting belt 100A. It is not necessary for the measurement subject to assume a face-up or a face-down position to stabilize that contact. The measurement subject 400 can therefore easily measure body fat or the like at home without help from an assistant or the like.

According to the body fat measurement device 1A, a body fat mass, such as the visceral fat mass, the subcutaneous fat mass, or the like, can be measured in a state in which the back area electrodes BU1-BU4 and BL1-BL4 are brought into contact with the measurement subject's back area surface. According to the body fat measurement device 1A, it is possible to apply a current locally to the back area, where the subcutaneous fat is relatively thicker, rather than applying a current locally to the abdominal area, where the subcutaneous fat is relatively thinner, which in turn makes it possible to measure the body fat mass is a more accurate manner.

Therefore, according to the body fat measurement device 1A, a body fat mass, such as the visceral fat mass and the subcutaneous fat mass, can be measured easily and accurately at home. Using the body fat measurement device 1A makes it possible to obtain such indicators for health management on a daily basis.

Although the opening 141 is formed by the band-shaped member 142 in the fitting belt 100A of the body fat measurement device 1A, an opening may be provided directly in the belt portion 140 instead of providing the band-shaped member 142. In this case, the hanging member 360 of the upper limb unit 300A is configured to be insertable into that opening.

Instead of employing the band-shaped member 142 and the hanging member 360, surface fasteners that can engage with each other can be employed as the first and second engagement members, or magnets that can adhere to each other can be employed as the first and second engagement members.

First Variation on First Embodiment

Figure 8:
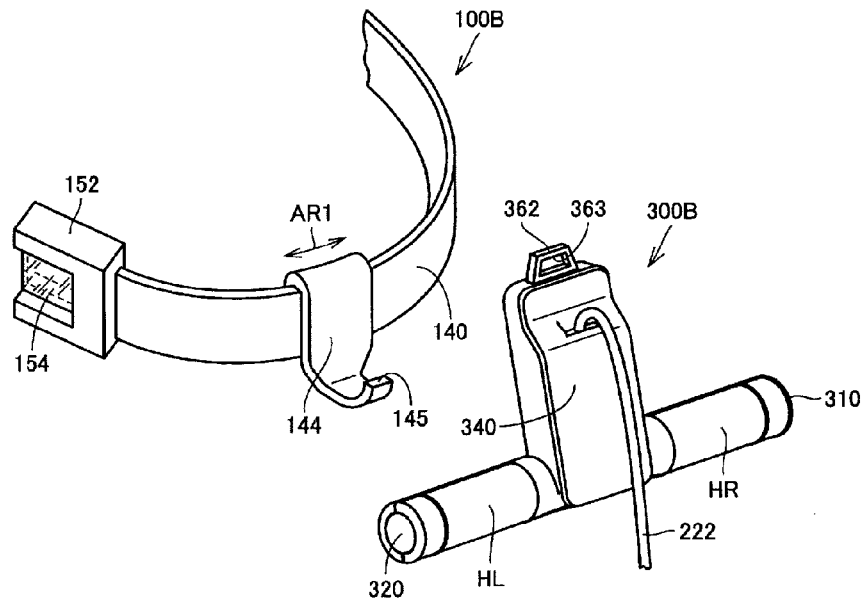
FIG. 8 is a perspective view illustrating a fitting belt and an upper limb unit according to a first variation on the first embodiment.

The present variation will be described with reference to FIG. 8. Here, only the differences from the body fat measurement device 1A according to the stated first embodiment will be described. A retaining member 144, serving as the first engagement member, is attached to the belt portion 140 in a fitting belt 100B according to the present variation. A hook portion 145 is provided on the leading end of the retaining member 144 so as to point upward. According to one or more embodiments of the present invention, the retaining member 144 is capable of moving freely along the lengthwise direction of the belt portion 140, as indicated by an arrow AR1.

A loop-shaped retained member 362, serving as the second engagement member, is provided in an upper limb unit 300B according to the present variation, on the base surface side of the main body unit 340. The retained member 362 may be provided on the upper surface side of the main body unit 340. An opening 363 provided in the retained member 362 is capable of engaging with the hook portion 145 of the retaining member 144. As a result of this engagement, the upper limb unit 300B is attached to the fitting belt 100B so as to hang down from the retaining member 144.

The measurement subject holds the fitting belt 100B to which the upper limb unit 300B is attached and steps onto the lower limb unit 200 (see FIG. 5). After the measurement subject has fitted the fitting belt 100B around his/her trunk area, s/he can remove the upper limb unit 300B from the fitting belt 100B while remaining in an erect position.

In the case where the retaining member 144 is capable of freely moving in the direction indicated by the arrow AR1, the position at which the upper limb unit 300B is attached to the fitting belt 100B is variable, improving the convenience for the measurement subject. Even with the body fat measurement device that includes the fitting belt 100B and the upper limb unit 300B, a body fat mass, such as the visceral fat mass and the subcutaneous fat mass, can be measured easily and accurately.

Second Variation on First Embodiment

Figure 9:
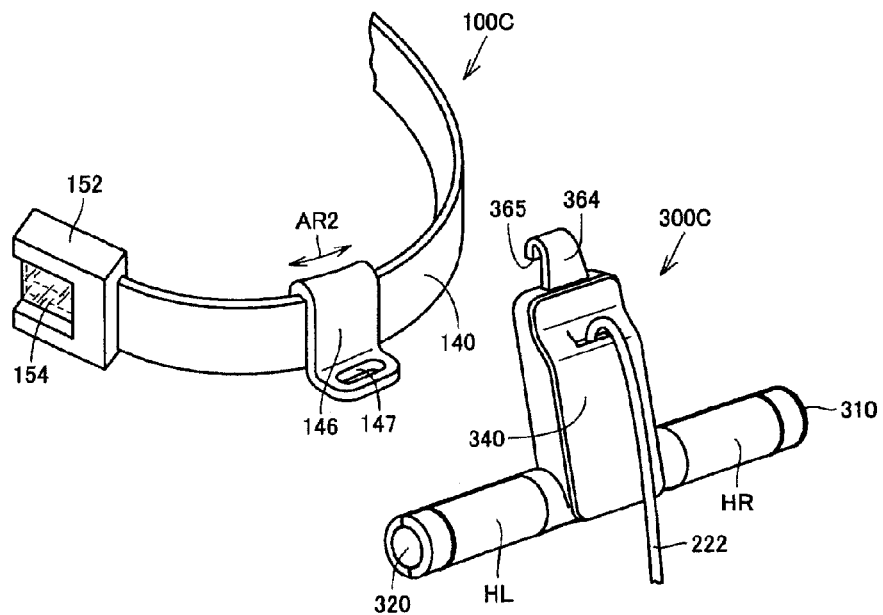
FIG. 9 is a perspective view illustrating a fitting belt and an upper limb unit according to a second variation on the first embodiment.

The present variation will be described with reference to FIG. 9. Here, only the differences from the body fat measurement device 1A according to the stated first embodiment will be described. A retained member 146, serving as the first engagement member, is attached to the belt portion 140 in a fitting belt 100C according to the present variation. An opening 147 is provided on the leading end of the retained member 146. According to one or more embodiments of the present invention, the retained member 146 is capable of moving freely along the lengthwise direction of the belt portion 140, as indicated by an arrow AR2.

A retaining member 364, serving as the second engagement member, is provided in an upper limb unit 300C according to the present variation, on the base surface side of the main body unit 340. The retaining member 364 may be provided on the upper surface side of the main body unit 340. A hook portion 365 provided in the leading end of the retaining member 364 is capable of engaging with the opening 147 of the retained member 146. As a result of this engagement, the upper limb unit 300C is attached to the fitting belt 100C so as to hang down from the retained member 146.

The measurement subject holds the fitting belt 100C to which the upper limb unit 300C is attached and steps onto the lower limb unit 200 (see FIG. 5). After the measurement subject has fitted the fitting belt 100C around his/her trunk area, s/he can remove the upper limb unit 300C from the fitting belt 100C while remaining in an erect position.

In the case where the retained member 146 is capable of freely moving in the direction indicated by the arrow AR2, the position at which the upper limb unit 300C is attached to the fitting belt 100C is variable, improving the convenience for the measurement subject. Even with the body fat measurement device that includes the fitting belt 100C and the upper limb unit 300C, a body fat mass, such as the visceral fat mass and the subcutaneous fat mass, can be measured easily and accurately.

Third Variation on First Embodiment

Figure 10:
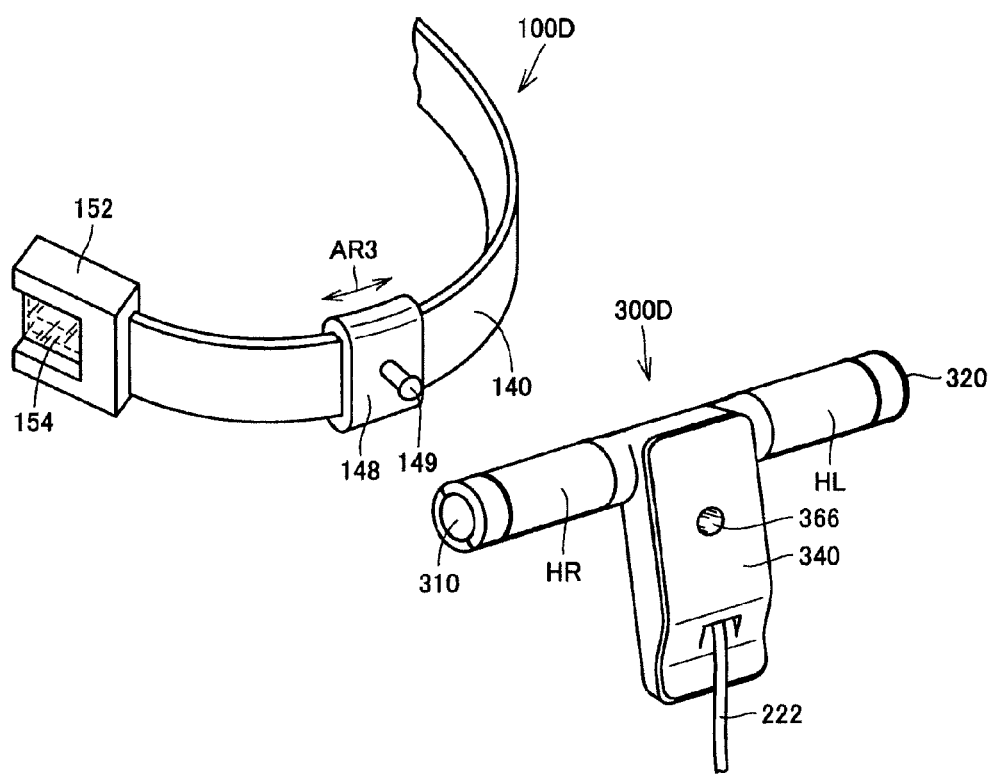
FIG. 10 is a perspective view illustrating a fitting belt and an upper limb unit according to a third variation on the first embodiment.

The present variation will be described with reference to FIG. 10. Here, only the differences from the body fat measurement device 1A according to the stated first embodiment will be described. A retaining member 148, serving as the first engagement member, is attached to the belt portion 140 in a fitting belt 100D according to the present variation. A pin 149 is provided on the surface of the retaining member 148 so as to protrude. According to one or more embodiments of the present invention, the retaining member 148 is capable of moving freely along the lengthwise direction of the belt portion 140, as indicated by an arrow AR3.

An opening 366, serving as the second engagement member, is formed in an upper limb unit 300D according to the present variation, on the rear surface side of the main body unit 340. The pin 149 can engage with the opening 366 by inserting the pin 149 into the opening 366. As a result of this engagement, the upper limb unit 300D is attached to the fitting belt 100D so as to hang down from the retaining member 148.

The measurement subject holds the fitting belt 100D to which the upper limb unit 300D is attached and steps onto the lower limb unit 200 (see FIG. 5). After the measurement subject has fitted the fitting belt 100D around his/her trunk area, s/he can remove the upper limb unit 300D from the fitting belt 100D while remaining in an erect position.

In the case where the retaining member 148 is capable of freely moving in the direction indicated by the arrow AR3, the position at which the upper limb unit 300D is attached to the fitting belt 100D is variable, improving the convenience for the measurement subject. Even with the body fat measurement device that includes the fitting belt 100D and the upper limb unit 300D, a body fat mass, such as the visceral fat mass and the subcutaneous fat mass, can be measured easily and accurately.

Second Embodiment

A body fat measurement device 1B according to the present embodiment will be described with reference to FIG. 11. Here, only the differences from the body fat measurement device 1A according to the stated first embodiment will be described. In the present embodiment, one end of the connection cable 222 is connected to the upper limb unit 300A, and the other end of the connection cable 222 is connected to the lower limb unit 200.

The measurement subject holds the fitting belt 100A to which the upper limb unit 300A is attached and steps onto the lower limb unit 200. After the measurement subject has fitted the fitting belt 100A around his/her trunk area, s/he can remove the upper limb unit 300A from the fitting belt 100A while remaining in an erect position. Even with the body fat measurement device 1B, a body fat mass, such as the visceral fat mass and the subcutaneous fat mass, can be measured easily and accurately.

Figure 11:
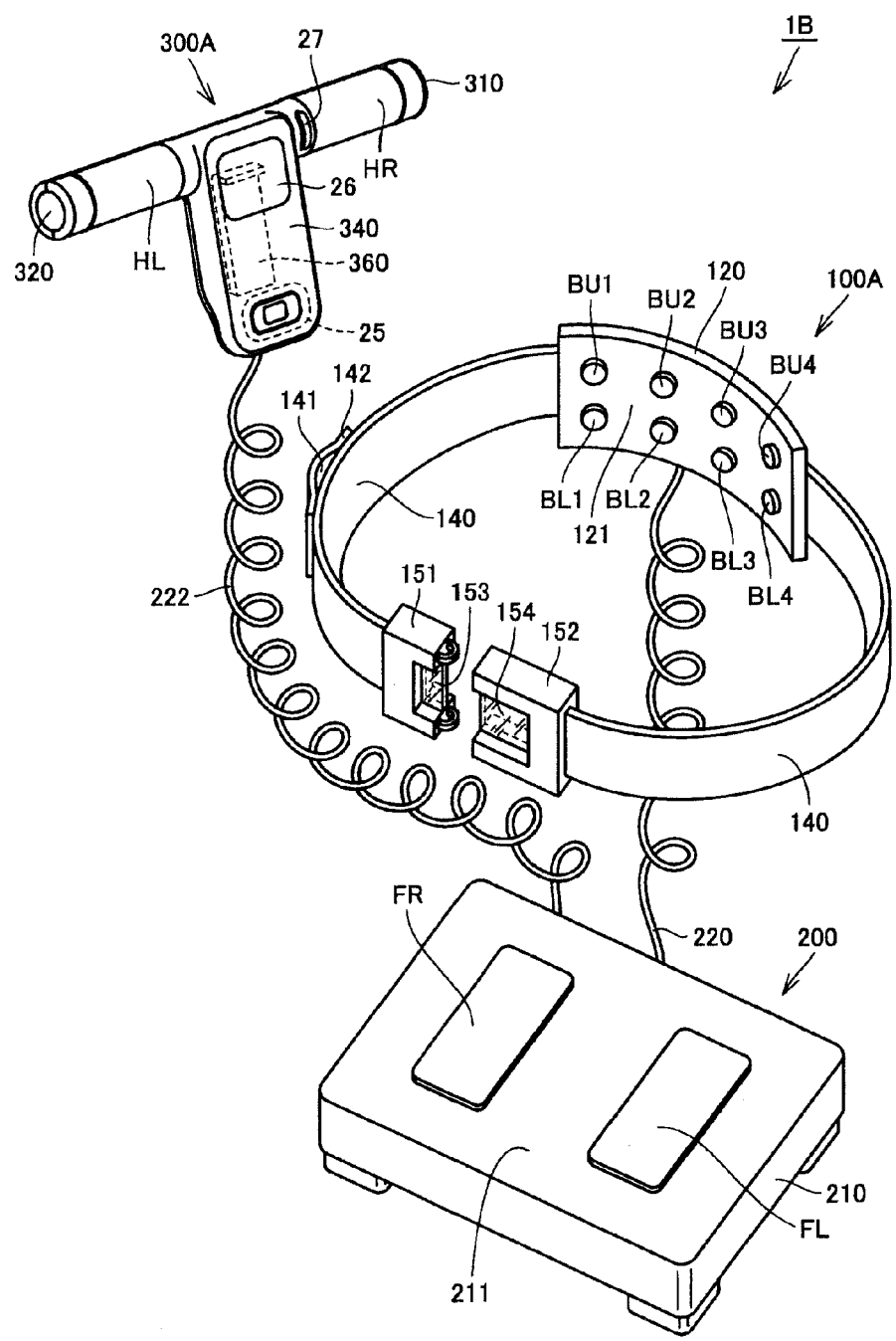
FIG. 11 is a perspective view illustrating a body fat measurement device according to a second embodiment.

The connection cable 222 is not limited to the so-called coiled shape shown in FIG. 11, and may be configured so as to be taken up into a reel member (not shown) provided in the lower limb unit 200.

First Variation on Second Embodiment

A body fat measurement device 1C according to the present variation will be described with reference to FIG. 12. Here, only the differences from the body fat measurement device 1B according to the stated second embodiment will be described. In the present variation, one end of the connection cable 220 is connected to the upper limb unit 300A, and the other end of the connection cable 220 is connected to the back area electrodes BU1-BU4 and BL1-BL4 of the fitting belt 100A.

The measurement subject holds the fitting belt 100A to which the upper limb unit 300A is attached and steps onto the lower limb unit 200. After the measurement subject has fitted the fitting belt 100A around his/her trunk area, s/he can remove the upper limb unit 300A from the fitting belt 100A while remaining in an erect position. Even with the body fat measurement device 1C, a body fat mass, such as the visceral fat mass and the subcutaneous fat mass, can be measured easily and accurately.

Figure 12:
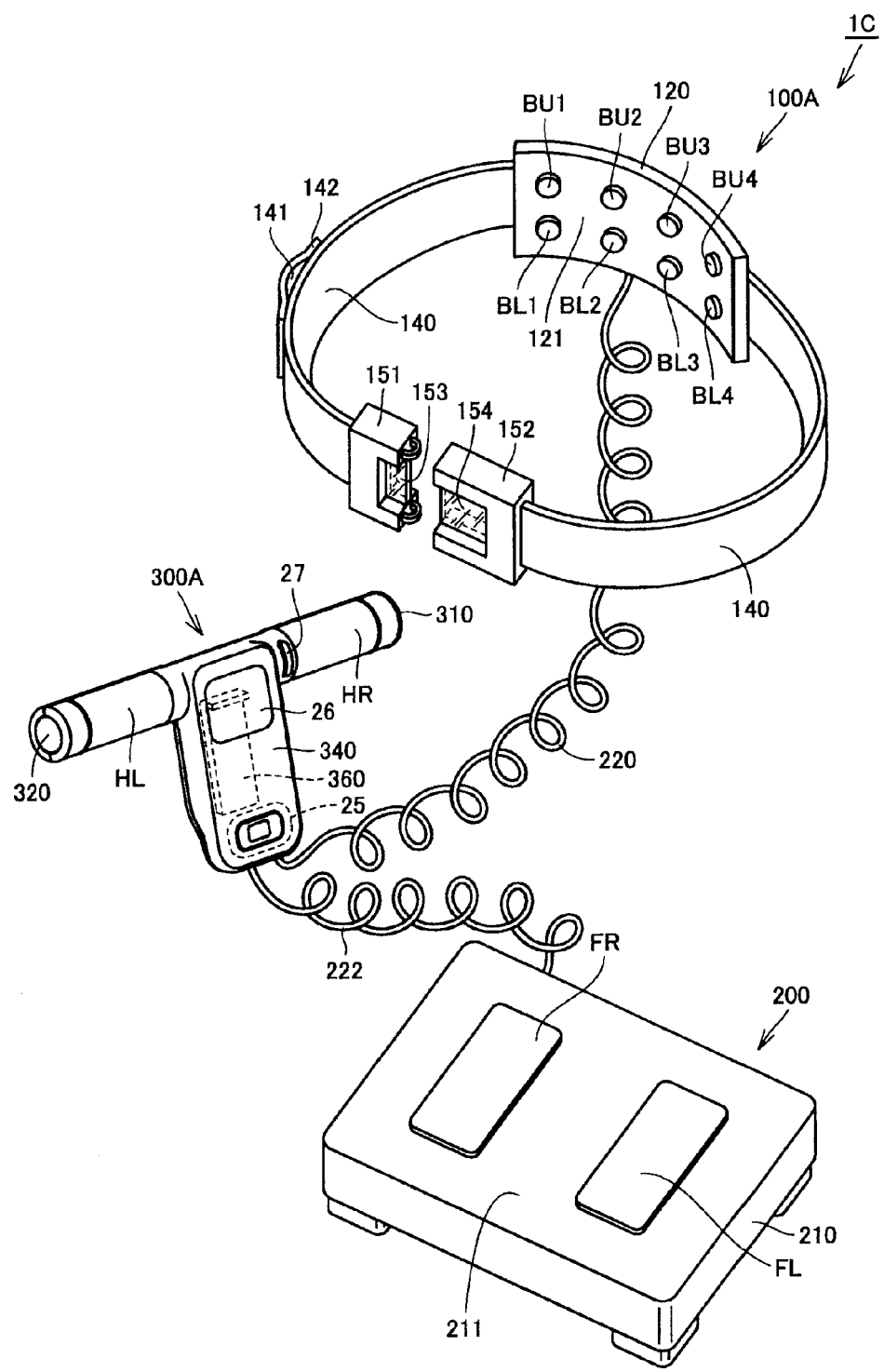
FIG. 12 is a perspective view illustrating a body fat measurement device according to a first variation on the second embodiment.

The connection cable 220 is not limited to the so-called coiled shape shown in FIG. 12, and may be configured so as to be taken up into a reel member (not shown) provided in the upper limb unit 300A.

Second Variation on Second Embodiment

A body fat measurement device 1D according to the present variation will be described with reference to FIG. 13. Here, only the differences from the body fat measurement device 1A according to the stated first embodiment will be described. In the present variation, a connector 225 is attached to one end of the connection cable 220. A connector 227 is attached to the other end of the connection cable 220. A connector 223 is attached to one end of the connection cable 222. A connector 221 is attached to the other end of the connection cable 222.

By using the connectors 221, 223, 225, and 227, the connections between the connection cables 220 and 222 and the upper limb unit 300A, the back area electrodes BU1-BU4 and BL1-BL4 in the fitting belt 100A, the buckle portion 151 in the fitting belt 100A, and the lower limb unit 200 can be disconnected and reconnected.

Figure 13:
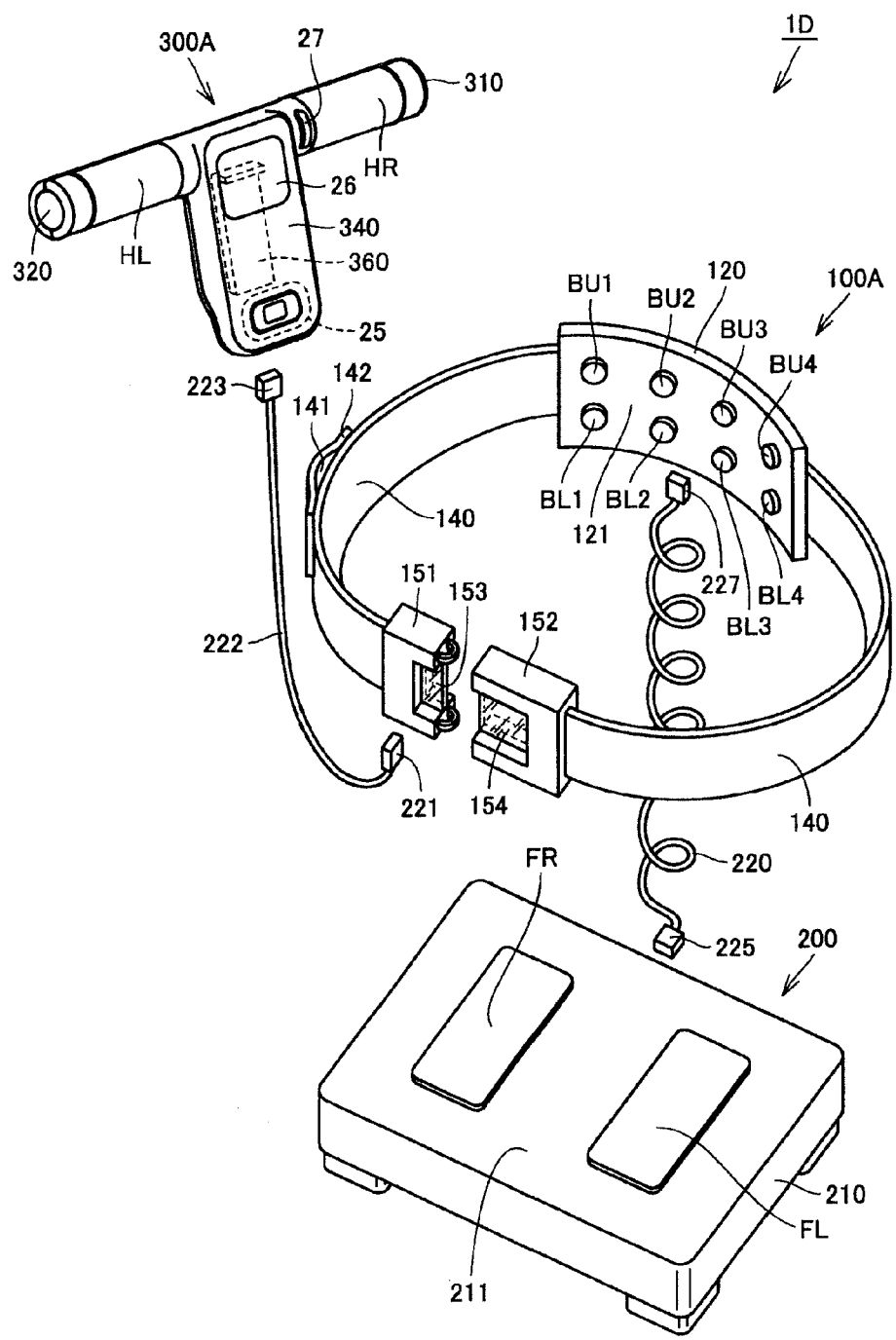
FIG. 13 is a perspective view illustrating a body fat measurement device according to a second variation on the second embodiment.

For example, as shown in FIG. 13, an electrical hard-wired connection can be established between one end of the connection cable 220 and the lower limb unit 200 using the connector 225. Likewise, the other end of the connection cable 220 can be electrically connected to the back area electrodes BU1-BU4 and BL1-BL4 in the upper limb unit 300A using the connector 227.

One end of the connection cable 222 can be electrically connected to the upper limb unit 300A using the connector 223. The other end of the connection cable 222 can be electrically connected to the buckle portion 151 in the fitting belt 100A using the connector 221.

Using the connectors 221, 223, 225, and 227, the connection cables 220 and 222 may be connected as in the body fat measurement device 1B according to the aforementioned first variation on the second embodiment (see FIG. 11), or may be connected as in the body fat measurement device 1C according to the aforementioned second variation on the second embodiment (see FIG. 12).

The measurement subject holds the fitting belt 100A to which the upper limb unit 300A is attached and steps onto the lower limb unit 200. After the measurement subject has fitted the fitting belt 100A around his/her trunk area, s/he can remove the upper limb unit 300A from the fitting belt 100A while remaining in an erect position. Even with the body fat measurement device 1D, a body fat mass, such as the visceral fat mass and the subcutaneous fat mass, can be measured easily and accurately.

Third Embodiment

A body fat measurement device 1E according to the present embodiment will be described with reference to FIG. 14. The fundamentals of the measurement performed by the body fat measurement device 1E and the computation processes executed by the control unit are the same as those of the body fat measurement device 1A according to the aforementioned first embodiment.

Like the body fat measurement device 1A according to the aforementioned first embodiment, the body fat measurement device 1E includes the fitting belt 100B, which can be disposed so as to surround the measurement subject's trunk area in a fitted state. However, unlike the body fat measurement device 1A according to the aforementioned first embodiment, the body fat measurement device 1B does not include a platform-shaped lower limb unit onto which the measurement subject can step; instead, electrode pads 125A and 125B, serving as extending unit portions configured so as to be extendable from the fitting belt 100B, are provided.

The electrode pads 125A and 125B have approximate plate shapes, and foot/hip electrodes FL' and FR', serving as lower limb/hip electrodes for making contact with the surface of the respective lower limbs or hips, are provided in an exposed state on the main surfaces of the electrode pads 125A and 125B, respectively. The one ends of connection cables 126A and 126B are attached to upper areas of the electrode pads 125A and 125B, respectively, and the other ends of the connection cables 126A and 126B are anchored to reel members (not shown) provided within the electrode support member 120.

In the fitting belt 100B, the electrode support member 120 is configured as a block-shaped member in order to make it possible to dispose the stated reel members within the electrode support member 120, and the electrode support member 120 is attached in approximately the center of the belt portion 140.

Figure 14:
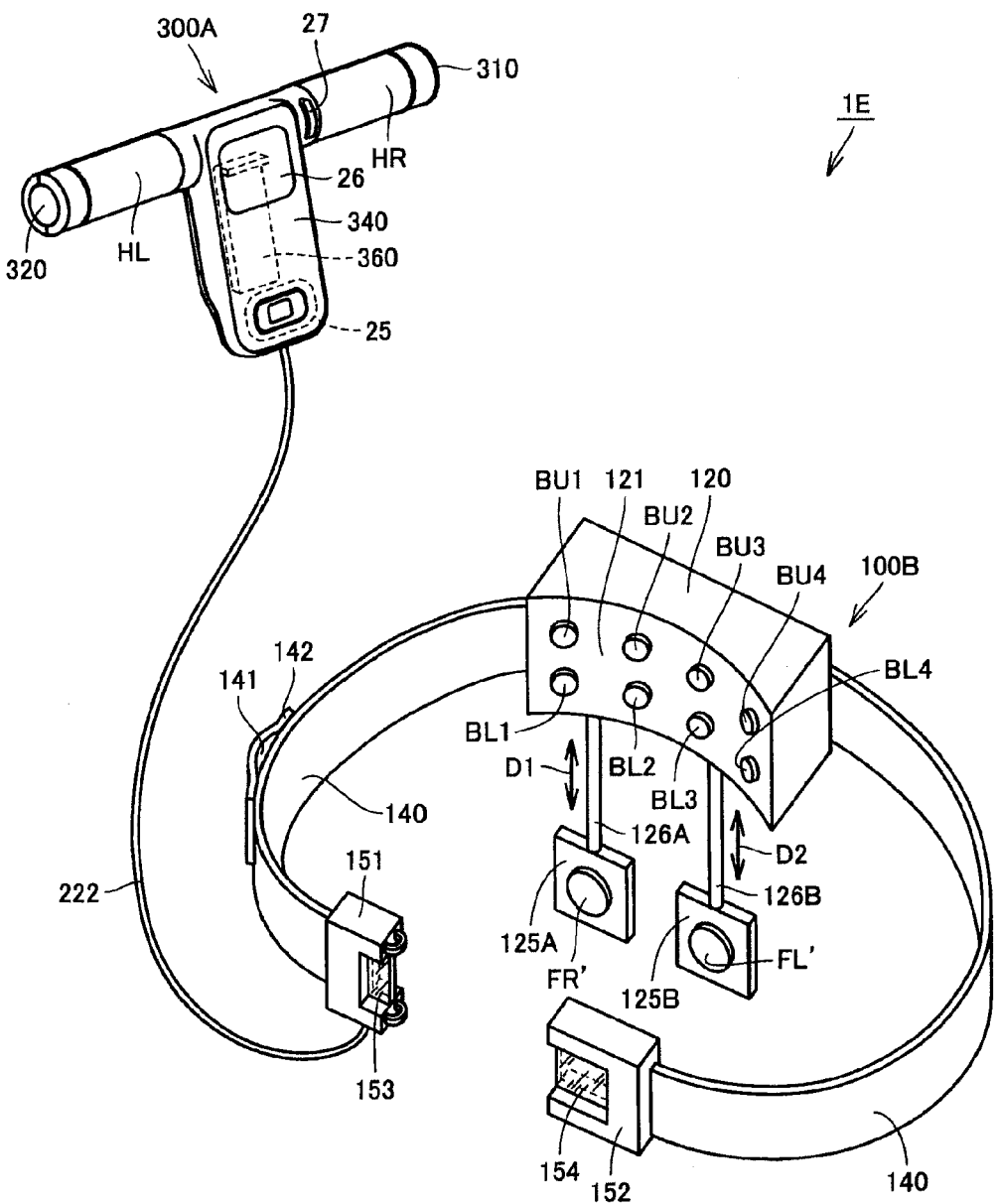
FIG. 14 is a perspective view illustrating a body fat measurement device according to a third embodiment.

Through this, the electrode pads 125A and 125B can be extended downward from the fitting belt 100B by pulling the connection cables 126A and 126B, which serve as connection lines, in the direction of arrows D1 and D2 shown in FIG. 14. By adjusting the extension amount of the connection cables 126A and 126B, the electrode pads 125A and 125B can be attached at desired locations, such as the lower limbs, the hips, and so on of the measurement subject.

Even with the body fat measurement device 1E, the same effects as the effects described above in the first embodiment can be achieved. In addition, the measurement can be carried out in a seated position as well as a standing position, which makes it even easier to measure the body fat mass. With the body fat measurement device 1E, there is no lower limb unit, and thus the device configuration can be simplified and the size of the device can be reduced.

Pads that attach to the measurement subject's body through suction, through an adhesive, or that are attached by being wrapped around the measurement subject's body using some sort of wrapping member can be used as the electrode pads 125A and 125B; furthermore, pads that are not particularly attached but are anchored by being sandwiched between the measurement subject's body and a seating surface, a floor surface, or the like can be used as the electrode pads 125A and 125B.

Fourth Embodiment

Fundamentals of Measurement Performed by Body Fat Measurement Device 1F

Figure 15:
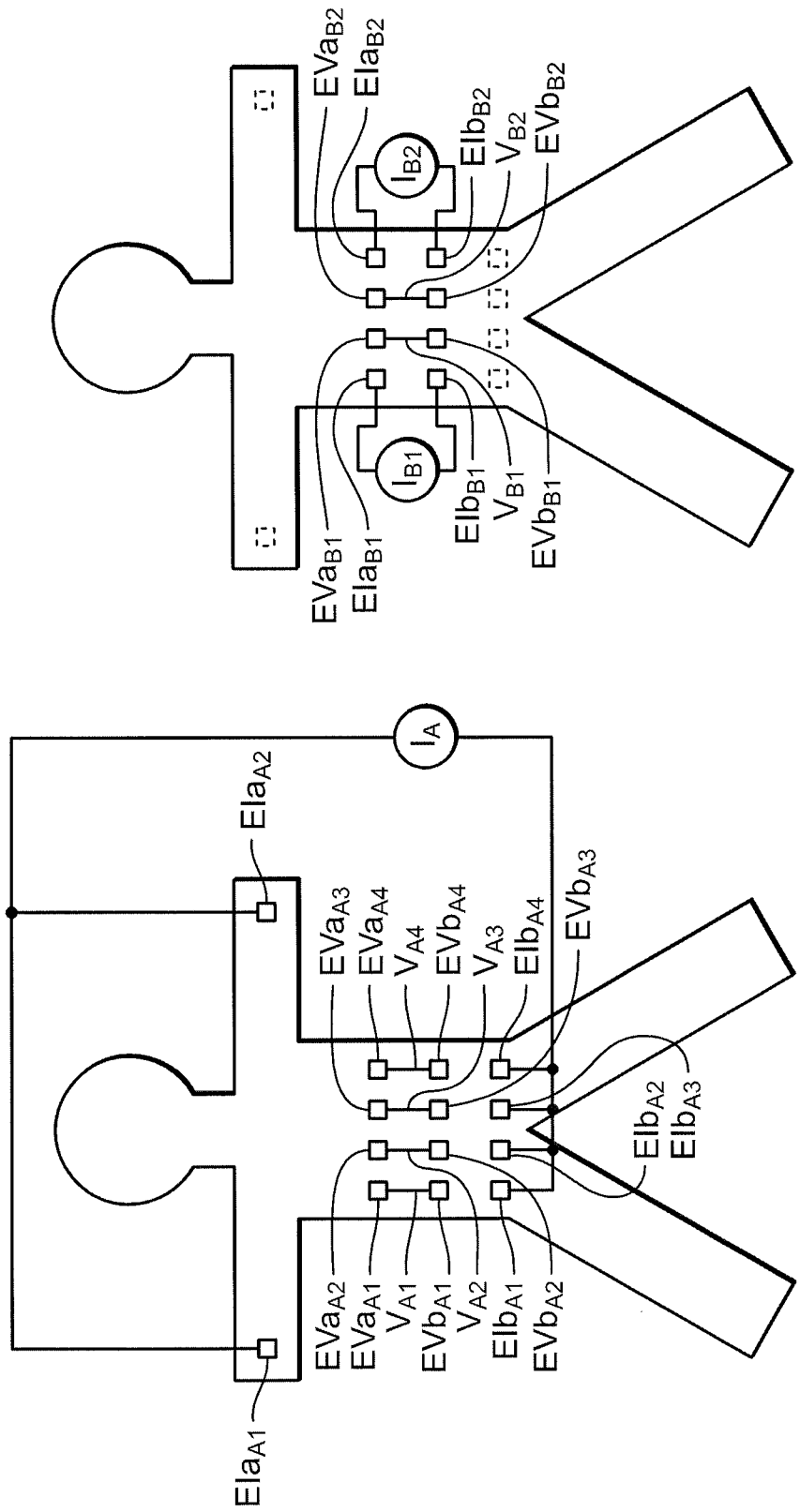
FIGS. 15A and 15B are diagrams illustrating the fundamentals of measurement performed by a body fat measurement device according to a fourth embodiment.

FIG. 15A is a diagram illustrating the placement of electrodes when obtaining a body impedance for the entire trunk area, whereas FIG. 15B is a diagram illustrating the placement of electrodes when obtaining a body impedance for a surface layer area on the back area side of the trunk area. FIGS. 15A and 15B both illustrate the measurement subject from the back side thereof. The fundamentals of measurement performed by a body fat measurement device 1F (see FIG. 17) according to the present embodiment will be described with reference to FIGS. 15A and 15B.

The fundamentals of the measurement performed by the body fat measurement device 1F are basically the same as the fundamentals of the measurement described in the aforementioned first embodiment (see FIG. 2). However, the positions in which the electrodes used when obtaining the body impedance of the entire trunk area are placed are different from those in the aforementioned first embodiment. As shown in FIG. 15A, electrodes $EIa_{A1}$ and $EIa_{A2}$ are attached to the surface of the left hand of the measurement subject and the surface of the right hand of the measurement subject, respectively, in order to obtain the body impedance for the entire trunk area.

Four pairs of electrodes are attached to the back area surface of the measurement subject, with each pair disposed so as to follow the body axis direction, and with the four pairs arranged in the widthwise direction of the trunk area; furthermore, four electrodes are attached to an area of the back area surface that is closer to the hip area than the contact locations where the stated four pairs of electrodes are placed, with these four electrodes being arranged along the widthwise direction of the trunk area. In other words, as shown in FIG. 15A, a total of twelve electrodes, or electrodes $EVa_{A1}$, $EVb_{A1}$, $EVa_{A2}$, $EVb_{A2}$, $EVa_{A3}$, $EVb_{A3}$, $EVa_{A4}$, $EVb_{A4}$, $EIb_{A1}$, $EIb_{A2}$, $EIb_{A3}$, and $EIb_{A4}$, are attached to the back area surface of the measurement subject.

In this state, a constant current $I_A$ that passes through the trunk area is applied to the measurement subject using the electrodes $EIa_{A1}$, $EIa_{A2}$, $EIb_{A2}$, $EIb_{A2}$, $EIb_{A3}$, and $EIb_{A1}$. While the constant current $I_A$ is being applied, the potential difference $V_{A1}$ is detected using the electrodes $EVa_{A1}$ and $EVb_{A1}$, the potential difference $V_{A2}$ is detected using the electrodes $EVa_{A2}$ and $EVb_{A2}$, the potential difference $V_{A3}$ is detected using the electrodes $EVa_{A3}$ and $EVb_{A3}$, and the potential difference $V_{A4}$ is detected using the electrodes $EVa_{A4}$ and $EVb_{A4}$.

A body impedance Zt of the entire trunk area is calculated from the potential differences $V_{A1}$, $V_{A2}$, $V_{A3}$, and $V_{A4}$. Note that the placement of electrodes, the constant current application, and the potential difference detection for obtaining the body impedance Zs of the surface layer area on the back area of the trunk area are, as shown in FIG. 15B, all the same as those in the aforementioned first embodiment.

Functional Blocks of Body Fat Measurement Device 1F

Figure 16:
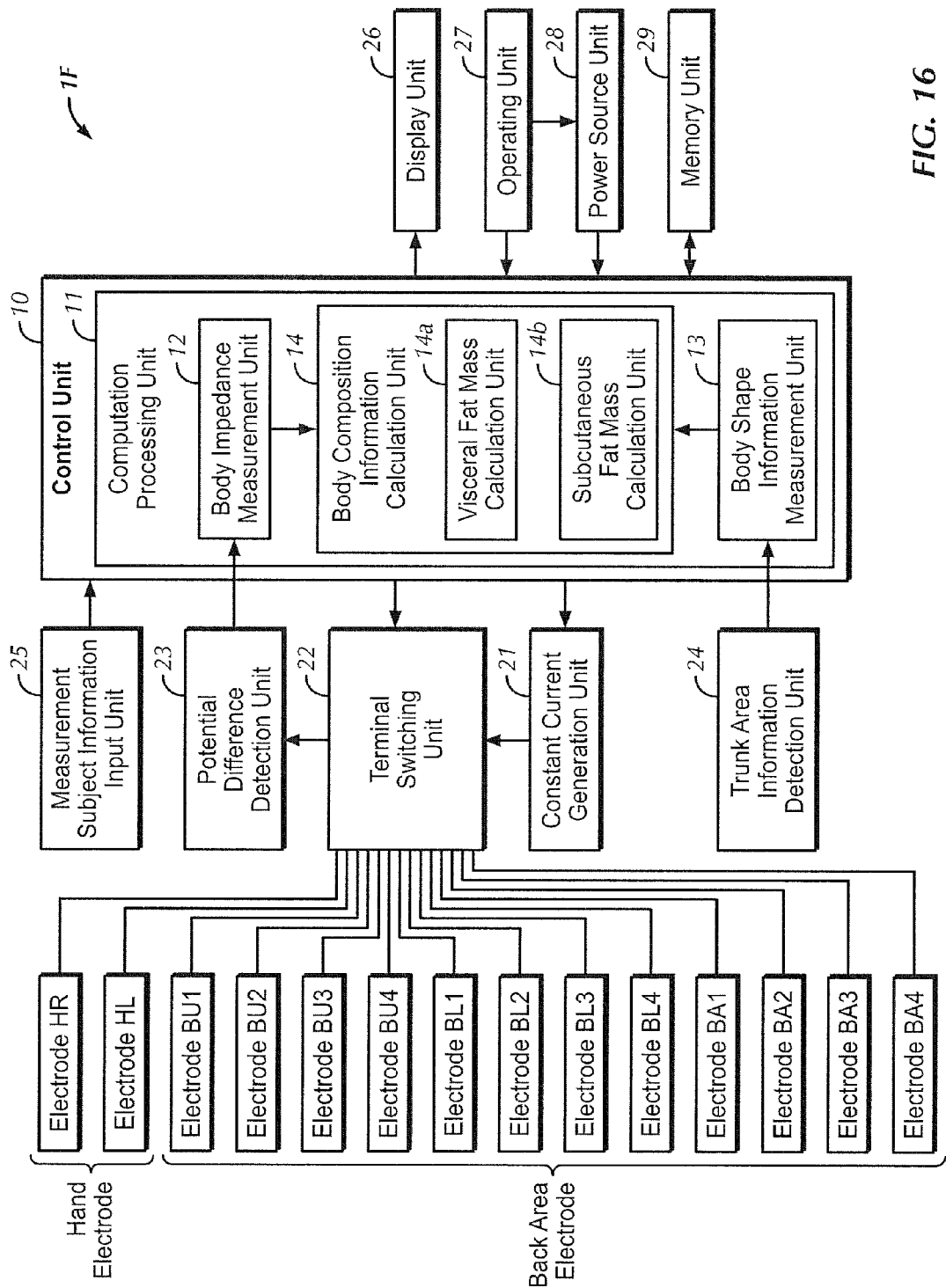
FIG. 16 is a diagram illustrating the functional block configuration of the body fat measurement device according to the fourth embodiment.

FIG. 16 is a diagram illustrating the functional block configuration of the body fat measurement device 1F according to the present embodiment. The functional block configuration of the body fat measurement device 1F will be described with reference to FIG. 16.

The body fat measurement device 1F has a similar configuration as the body fat measurement device 1A according to the aforementioned first embodiment, but differs slightly in terms of the configuration of the multiple electrodes connected to the terminal switching unit 22. The body fat measurement device 1F includes electrodes HR, HL, BU1-BU4, BL1-BL4, and BA1-BA4 as the multiple electrodes.

The aforementioned multiple electrodes include: hand electrodes HR and HL serving as upper limb electrodes placed in contact with surfaces of the upper limbs of the measurement subject; and back area electrodes BU1-BU4, BL1-BL4, and BA1-BA4 placed in contact with the back area surface of the measurement subject. Of these, the hand electrodes HR and HL are placed in contact with the palms of the measurement subject's hands. As shown in FIGS. 15A and 15B, the back area electrodes BU1-BU4, BL1-BL4, and BA1-BA4 are arranged in rows and placed in contact with the back area surface of the measurement subject. The hand electrodes HR and HL and the back area electrodes BU1-BU4, BL1-BL4, and BA1-BA4 are all electrically connected to the terminal switching unit 22 described above.

Structure of Body Fat Measurement Device 1F

Figure 17:
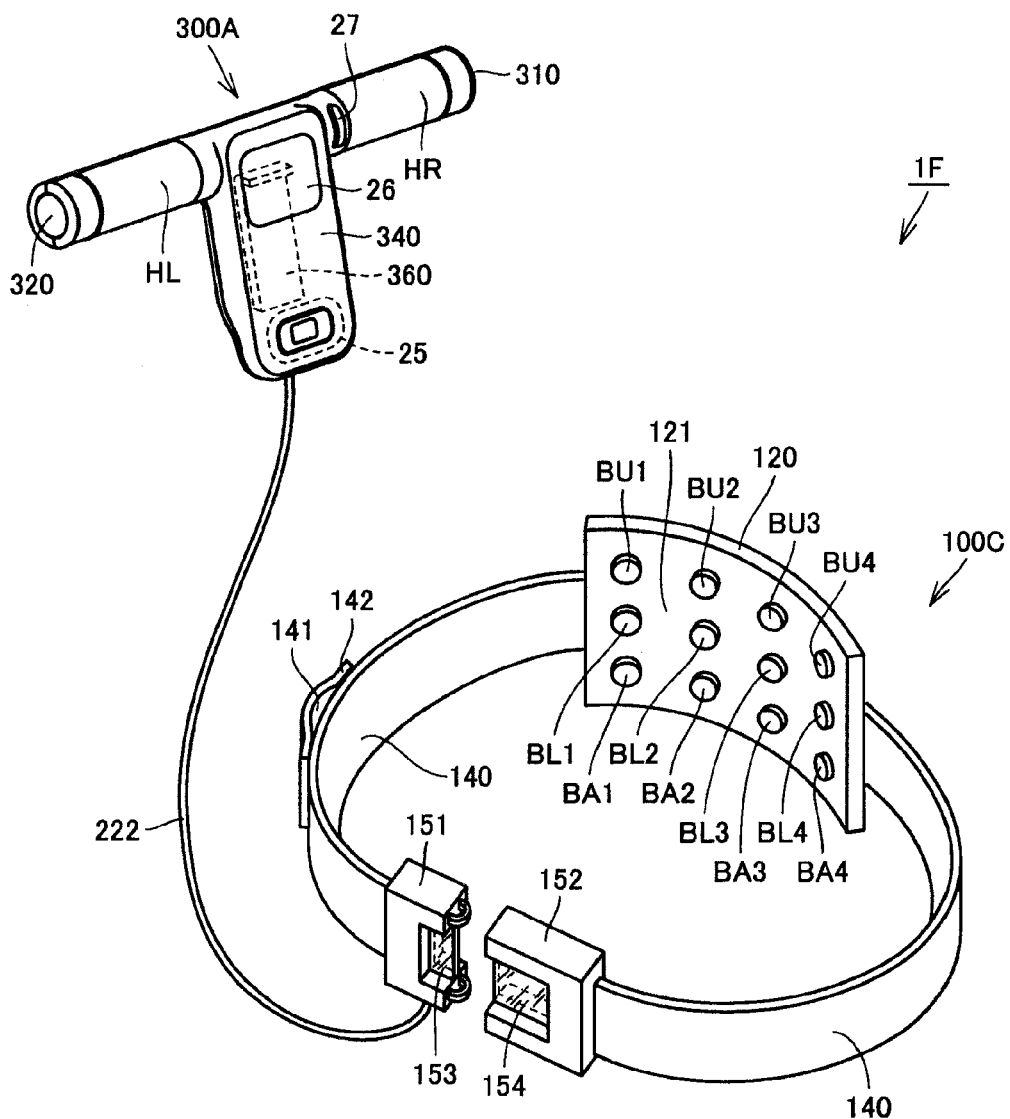
FIG. 17 is a perspective view illustrating the body fat measurement device according to the fourth embodiment.

FIG. 17 is a perspective view illustrating the body fat measurement device 1F according to the present embodiment. Like the body fat measurement device 1A according to the aforementioned first embodiment of the present invention, the body fat measurement device 1F includes the fitting belt 100C, which can surround the measurement subject's trunk area in a fitted state. However, unlike the body fat measurement device 1A according to the aforementioned first embodiment of the present invention, the body fat measurement device 1C does not include a platform-shaped lower limb unit onto which the measurement subject can step. With the body fat measurement device 1C, the back area electrodes BA1-BA4 are further provided on the electrode support member 120.

To be more specific, the electrode support member 120, which is configured of a curved plate, extends further downward than in the aforementioned first embodiment, and the back area electrodes BA1-BA4 are provided on the front surface 121 of the area of the electrode support member 120 that has been extended. The back area electrodes BA1-BA4 are provided so that all the electrodes are exposed on the front surface 121 of the electrode support member 120. According to one or more embodiments of the present invention, the back area electrodes BA1-BA4 protrude slightly from the front surface 121 of the electrode support member 120. Through this, the back area electrodes BA1-BA4 are, like the back area electrodes BU1-BU4 and BL1-BL4, placed in contact with the back area surface of the measurement subject during the fitted state.

Even with the body fat measurement device 1F, the same effects as the effects described above in the first embodiment of the present invention can be achieved. In addition, the measurement can be carried out in a seated position as well as a standing position, which makes it even easier to measure the body fat mass. With the body fat measurement device 1F, there is no lower limb unit, and thus the device configuration can be simplified and the size of the device can be reduced.

Although body fat measurement devices according to several embodiments of the present invention have been described, it should be noted that the embodiments disclosed above are to be understood as being in all ways exemplary and in no way limiting.

Although the aforementioned first through fourth embodiments and the variations thereon describe examples in which the computation processes are configured so as to calculate the visceral fat cross-sectional area as the visceral fat mass and the subcutaneous fat cross-sectional area as the subcutaneous fat mass, the computation processes may be configured so that a different indicator than the visceral fat cross-sectional area, such as the visceral fat volume, visceral fat weight, visceral fat level, or the like is calculated as the visceral fat mass, and a different indicator than the subcutaneous fat cross-sectional area, such as the subcutaneous fat volume, subcutaneous fat weight, subcutaneous fat level, or the like is calculated as the subcutaneous fat mass.

Although the aforementioned first through fourth embodiments and the variations thereon describe examples in which the configuration is such that both the visceral fat cross-sectional area and the subcutaneous fat cross-sectional area are calculated and displayed, the configuration may be such that only one of these indicators is displayed, or that only the subcutaneous fat cross-sectional area is calculated and displayed. Furthermore, the configuration may be such that various types of body composition information aside from the visceral fat cross-sectional area and the subcutaneous fat cross-sectional area (for example, the body fat mass, area-by-area fat mass, fat-free mass, and so on) are calculated and displayed.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1A-1F body fat measurement device
10 control unit
11 computation processing unit
12 body impedance measurement unit
13 body shape information measurement unit
14 body composition information calculation unit
14a visceral fat mass calculation unit
14b subcutaneous fat mass calculation unit
21 constant current generation unit
22 terminal switching unit
23 potential difference detection unit
24 trunk area information detection unit
25 measurement subject information input unit
26 display unit
27 operating unit
28 power source unit
29 memory unit
100A-100D fitting belt
120 electrode support member
121 front surface
125A, 125B electrode pad
126A, 126B, 220, 222 connection cable
140 belt portion
141, 147, 363, 366 opening
142 band-shaped member
144, 148, 364 retaining member
145, 365 hook portion
146, 362 retained member
149 pin
151, 152 buckle portion
153, 154 light-transmissive window portion
200 lower limb unit
210 platform portion
211 top surface
221, 223, 225, 227 connector
300A-300D, 300Aa, 300Ab upper limb unit
310 right-hand grip portion
320 left-hand grip portion
340 main body unit
360 hanging member
360a projection
400 measurement subject
401 right foot
402 left foot
403 right hand
404 left hand
405 trunk area
AR1-AR3, D1, D2 arrow
BA1-BA4, BL1-BL4, BU1-BU4 back area electrode
FR, FL foot electrode
FL', FR' foot/hip electrode
HR, HL hand electrode
S1-S13 step

The invention claimed is:

1. A body fat measurement device comprising:
a plurality of electrodes comprising back area electrodes for making contact with a surface of a back area that is an area on a back side of a trunk area of a measurement subject, and upper limb electrodes for making contact with a surface of upper limbs of the measurement subject;
a body impedance measurement unit for measuring a body impedance of the measurement subject's body using said plurality of electrodes;
a body composition information calculation unit that calculates a body fat mass based on said body impedance measured by said body impedance measurement unit;
a fitting belt for bringing said back area electrodes into contact with the surface of the back area of the measurement subject in a pressurized state by being tightened around the trunk area of the measurement subject; and
an upper limb unit comprising a gripping portion that can be gripped by a hand of the measurement subject, said upper limb electrodes being provided in said gripping portion,
wherein said upper limb unit can be attached to and detached from said fitting belt,
wherein the fitting belt comprises a buckle portion having a light-transmissive window portion,
wherein, when the fitting belt is tightened around the trunk area of the measurement subject, the fitting belt measures a circumferential length of the trunk area of the measurement subject,
wherein a surface of the light-transmissive window portion has a marker, and
wherein the light-transmissive window allows the measurement subject to visually check whether a position of a navel of the measurement subject matches a position of the marker.

2. The body fat measurement device according to claim 1, wherein said fitting belt comprises a first engagement member,
wherein said upper limb unit comprises a second engagement member that can engage with said first engagement member,
wherein said upper limb unit is attached to said fitting belt by said first engagement member entering an engaged state with said second engagement member, and
wherein said upper limb unit can be detached from said fitting belt by canceling said engaged state.

3. The body fat measurement device according to claim 2, wherein said first engagement member forms an opening by being attached to said fitting belt,
wherein said second engagement member has a predetermined length that enables said second engagement member to be inserted into said opening, wherein said upper limb unit is attached to said fitting belt by said second engagement member being inserted into said opening, and wherein said upper limb unit is detached from said fitting belt by said second engagement member being pulled out from said opening.

4. The body fat measurement device according to claim 2, wherein the position at which said first engagement member is attached to said fitting belt can be moved along a lengthwise direction of said fitting belt.

5. The body fat measurement device according to claim 1, wherein said upper limb unit further comprises a display unit that displays body composition information including said body fat mass calculated by said body composition information calculation unit.

6. The body fat measurement device according to claim 1, wherein said upper limb unit further comprises an operating unit for accepting an instruction from the measurement subject.

7. The body fat measurement device according to claim 1, wherein said plurality of electrodes further comprises lower limb electrodes for making contact with surfaces of lower limbs of the measurement subject, and wherein the body fat measurement device further comprises: a lower limb unit for bringing said lower limb electrodes into contact with soles of feet of the measurement subject when the measurement subject steps onto the lower limb unit.

8. The body fat measurement device according to claim 7, wherein said upper limb unit and said fitting belt are electrically connected to each other via a first wire, and wherein one of said upper limb unit or said fitting belt is electrically connected to said lower limb unit via a second wire.

9. The body fat measurement device according to claim 7, wherein connection cables that connect said upper limb unit, said fitting belt, and said lower limb unit can be connected to and disconnected from said upper limb unit, said fitting belt, and said lower limb unit.

10. The body fat measurement device according to claim 7, wherein said lower limb unit comprises a body weight measurement unit for measuring a weight of the measurement subject.

* * * * *